(12) United States Patent
Chung et al.

(10) Patent No.: US 11,617,796 B2
(45) Date of Patent: Apr. 4, 2023

(54) CONJUGATE OF MINOXIDIL AND PEPTIDE

(71) Applicant: CAREGEN CO., LTD., Anyang-si (KR)

(72) Inventors: Yong Ji Chung, Seoul (KR); Eun Mi Kim, Yongin-si (KR)

(73) Assignee: Caregen Co., Ltd., Anyang-si (KR)

( * ) Notice: Subject to any disclaimer, the term of this patent is extended or adjusted under 35 U.S.C. 154(b) by 107 days.

(21) Appl. No.: 16/326,618

(22) PCT Filed: Aug. 4, 2017

(86) PCT No.: PCT/KR2017/008428
§ 371 (c)(1),
(2) Date: Feb. 19, 2019

(87) PCT Pub. No.: WO2018/034453
PCT Pub. Date: Feb. 22, 2018

(65) Prior Publication Data
US 2019/0192677 A1   Jun. 27, 2019

(30) Foreign Application Priority Data

Aug. 19, 2016 (KR) .................... 10-2016-0105707

(51) Int. Cl.
| | |
|---|---|
| A61K 47/64 | (2017.01) |
| A61Q 7/00 | (2006.01) |
| C07K 7/08 | (2006.01) |
| A61K 31/506 | (2006.01) |
| C07K 7/06 | (2006.01) |
| A61K 47/50 | (2017.01) |
| C07K 19/00 | (2006.01) |
| A61K 8/49 | (2006.01) |
| A61P 17/14 | (2006.01) |
| A61K 8/64 | (2006.01) |
| A61K 9/00 | (2006.01) |
| A61K 31/513 | (2006.01) |
| A61K 38/17 | (2006.01) |

(52) U.S. Cl.
CPC ............... *A61K 47/64* (2017.08); *A61K 8/49* (2013.01); *A61K 8/4953* (2013.01); *A61K 8/64* (2013.01); *A61K 9/0014* (2013.01); *A61K 31/506* (2013.01); *A61K 31/513* (2013.01); *A61K 38/1709* (2013.01); *A61K 47/50* (2017.08); *A61P 17/14* (2018.01); *A61Q 7/00* (2013.01); *C07K 7/06* (2013.01); *C07K 7/08* (2013.01); *C07K 19/00* (2013.01); *A61K 2800/57* (2013.01); *Y02P 20/55* (2015.11)

(58) Field of Classification Search
CPC .......... A61L 9/0014; A61L 8/64; A61L 47/50; A61L 8/4953; A61L 8/49; A61L 31/513; A61L 38/1709; A61L 47/64; A61L 2800/57; A61L 31/506; C07K 7/06; C07K 19/00; C07K 7/08; Y02P 20/55; A61P 17/14; A61Q 7/00
See application file for complete search history.

(56) References Cited

U.S. PATENT DOCUMENTS

| | | | |
|---|---|---|---|
| 7,507,719 | B2 | 3/2009 | Pinel et al. |
| 8,497,241 | B2 | 7/2013 | Chung et al. |
| 8,501,689 | B2 | 8/2013 | Chung et al. |
| 8,729,028 | B2 | 5/2014 | Chung et al. |
| 9,295,629 | B2 | 3/2016 | Chung et al. |
| 2004/0142853 | A1 | 7/2004 | Patt |
| 2004/0191203 | A1 | 9/2004 | Mahe |
| 2007/0004633 | A1 | 1/2007 | Pinel et al. |
| 2007/0224150 | A1 | 9/2007 | Chung |
| 2009/0081145 | A1 | 3/2009 | Knorr et al. |
| 2010/0310637 | A1 * | 12/2010 | Abdulrazik ............ A61K 38/28 424/450 |
| 2011/0160131 | A1 | 6/2011 | Chung et al. |
| 2011/0293526 | A1 | 12/2011 | Plikus et al. |
| 2011/0306546 | A1 | 12/2011 | Armani et al. |
| 2011/0312884 | A1 | 12/2011 | Chung et al. |
| 2012/0238498 | A1 | 9/2012 | Endo |
| 2012/0245086 | A1 | 9/2012 | Chung et al. |

(Continued)

FOREIGN PATENT DOCUMENTS

| | | | |
|---|---|---|---|
| CA | 2277946 A1 * | 7/1998 | .............. A61P 17/14 |
| CN | 102027008 A | 4/2011 | |

(Continued)

OTHER PUBLICATIONS

Jain et al, Mutual prodrugs containing bio-cleavable and drug releasable disulfide linkers, Bioorganic Chemistry, 2013, 49, pp. 40-48.*
Hairloss, from https://www.mayoclinic.org/diseases-conditions/hair-loss/symptoms-causes/syc-20372926 . . . , pp. 1-4, accessed Jul. 31, 2020.*
Alopecia, from Merck Manual, Sep. 2019, pp. 1-10.*
Insulin-levels of structure, from https://biotopics.co.uk/as/insulinproteinstructure.html, pp. 1-4, accessed Aug. 4, 2020.*
Hormones, from http://www.uwyo.edu/cmdelrio/site/teaching_files/12%20(2013).pptx, 2013, pp. 1-50.*

(Continued)

*Primary Examiner* — Li N Komatsu
(74) *Attorney, Agent, or Firm* — Merchant & Gould P.C.

(57) ABSTRACT

The present invention relates to a composition for preventing hair loss and, more specifically, to a compound having a structure in which Minoxidil and a peptide are chemically connected, and to a pharmaceutical composition or cosmetic composition for preventing hair loss or promoting hair growth comprising the compound. The compound having a structure in which Minoxidil and a peptide are chemically connected according to the present invention has not only excellent physiological activity such as hair loss reduction, hair growth promotion or cell growth promotion, but also excellent stability in water, and can therefore be useful as a composition for preventing hair loss and promoting hair growth.

10 Claims, 15 Drawing Sheets
Specification includes a Sequence Listing.

(56) References Cited

U.S. PATENT DOCUMENTS

| 2014/0309157 A1 | 10/2014 | Chung et al. |
| 2016/0272679 A1 | 9/2016 | Chung et al. |

FOREIGN PATENT DOCUMENTS

| CN | 102348716 A | 2/2012 |
| CN | 103547282 A | 1/2014 |
| EP | 1103545 A1 | 5/2001 |
| EP | 2383283 A2 | 11/2011 |
| EP | 2740741 A1 | 6/2014 |
| EP | 2275440 B1 | 12/2016 |
| JP | 4-506203 A | 10/1992 |
| JP | 2005-508873 A | 4/2005 |
| JP | 2011-519358 A | 7/2011 |
| JP | 2012-515769 A | 7/2012 |
| JP | 2013-010769 A | 1/2013 |
| JP | 2013-503856 A | 2/2013 |
| KR | 10-2009-0108323 A | 10/2009 |
| KR | 10-2010-0085407 A | 7/2010 |
| KR | 10-2011-0023991 A | 3/2011 |
| KR | 10-2012-0011632 A | 2/2012 |
| KR | 10-2013-0015530 A | 2/2013 |
| KR | 10-2017-0027312 A | 3/2017 |
| KR | 10-2019-0009402 A | 1/2019 |
| WO | 2004/043415 A1 | 5/2004 |
| WO | 2005/092850 A1 | 10/2005 |
| WO | 2007/076993 A1 | 7/2007 |
| WO | 2007/113687 A2 | 10/2007 |
| WO | 2010/059861 A1 | 5/2010 |

OTHER PUBLICATIONS

International Search Report and Written Opinion from International Application No. PCT/KR2017/008428, dated Sep. 22, 2017.
R. B. Merrifield: "Solid Phase Peptide Synthesis. I. The Synthesis of a Tetrapeptide", J. Am. Chem. Soc., 1963, 85 (14), pp. 2149-2154.
Cheng-Lung Hsu et al: "Minoxidil may suppress androgen receptor-related functions", Oncotarget, vol. 5, No. 8, pp. 2187-2197 (Apr. 8, 2014).
Extended European Search Report from European Patent Application No. 17841636.8, dated Jun. 17, 2019.
ARIPO Office Action for ARIPO Application No. AP/P/2019/011432 dated Aug. 15, 2021 (4 pages).
Chinese Office Action for CN Application No. 201780057559.X dated Sep. 8, 2021 (11 pages, with English translation).
Shiosaki et al., "Development of Potent and Selective CCK—A Receptor Agonists from Boc-CCK-4: Tetrapeptides Containing Lys(N')-Amide Residues," J. Med. Chem., 1992, 35:2007-2014.

* cited by examiner

CONJUGATE OF MINOXIDIL AND PEPTIDE

This application is a National Stage Application of International Application No. PCT/KR2017/008428, filed 4 Aug. 2017, which claims benefit of Serial No. 10-2016-0105707, filed 19 Aug. 2016 in the Republic of Korea and which applications are incorporated herein by reference. To the extent appropriate, a claim of priority is made to each of the above disclosed applications.

TECHNICAL FIELD

The present invention relates to a conjugate of Minoxidil and peptide, and more particularly, to a conjugate of Minoxidil and peptide in which each activity synergizes with each other while retaining the respective properties of Minoxidil and peptide.

BACKGROUND ART

A hair follicle is a unique organ of mammalian skin, which is formed by growing and extending of the lower part of the primitive epidermis into a deeper skin layer. The plug of cells known as saccule or dermal papilla exists in the base of the hair follicle, and papilla is essential in normal circulation of the hair follicle and in growth of the hair shaft. The hair shaft has a thread-shaped structure formed by epithelial cells that are composed of keratin filaments and filament-aggregating proteins tightly attached thereto.

Human hair periodically repeats anagen, catagen, and telogen phases, and goes through the process of hair loss and regeneration. The hair cycle is determined by hormone regulation and many growth factors, and hair enters the telogen phase early through the catagen phase by severe stress or malnutrition and causes severe hair loss symptoms.

The loss phenomenon of hair from the scalp is called hair loss, and factors affecting hair loss may include environmental factors such as climate, exposure to light or heat, and internal factors such as disease, birth, hormone secretion and changes, drug use, and nutritional status. Hair loss can also be caused by lack of nutrition, scalp drying, stress, etc. in addition to enzymatic action. In the case of hair loss due to such causes, hair loss can be prevented by sufficient nutrition supply, scalp management and ingestion or administration of antioxidants while hair growth can be promoted.

In order to treat such hair loss phenomenon, various materials have been used as medicines until now, but they had the disadvantage that the price was too expensive or the individual differences in efficacy were too high. For other cosmetic products, they have used botanical extracts which are cheaper but have little effect, and thus the effect was insignificant. A typical example of a drug used for hair loss is Minoxidil. The Minoxidil has been approved by the US FDA and has been reported to have an activity of inducing the anagen phase from the hair cycle of the telogen phase and maintaining the hair cycle of the induced anagen phase, besides the vasodilator function as a unique potassium channel opener. However, the Minoxidil may, when used, delay hair loss, but could not actually be used to induce regeneration of new hair follicles. In addition, the Minoxidil has a low solubility in water and thus is precipitated and is difficult to use. To solve these problems, Patent Document 1 (Korean Laid-open Patent Publication No. 10-2012-0011632) discloses a technique of adding a surfactant when using the Minoxidil.

Meanwhile, there are many factors linked to each other in the process of hair growth and degeneration. For example, a study has been reported using a series of growth factors to promote hair growth by promoting the growth factor of the keratinocyte, promoting the activity of the vascular endothelial growth factor, promoting the WINT pathway, and inhibiting the activity of proteins involved in the BMP pathway. However, the growth factors are highly effective, but require additional processing and time for refolding to obtain a natural growth factor, and also require a complex purification process to remove contaminants from $E.\ coli$ during the purification process, and is less useful because of its stability and its high molecular weight and thus its inability to easily jump over the hair's protective membrane in combination with high price.

Accordingly, the inventors of the present invention have developed peptides that can perform the same or similar functions or actions as natural growth factors, but have better stability than the natural growth factors and can overcome problems caused by the large molecular weight of the natural growth factors, that is, a Nokkin peptide composed of the amino a WINT peptide consisting of the amino acid sequence of SEQ ID NO: 3 (Patent Document 2: Korean Laid-5 open Patent Publication No. 10-2010-0085407), a Keramin2 peptide consisting of the amino acid sequence of SEQ ID NO: 2 (Patent Document 3: Korean Laid-open Patent Publication No. 10-2009-0108323) and a Nokkin peptide consisting of the amino acid sequence of SEQ ID NO: 1 (Patent Document 4: Korean Laid-open Patent Publication No. 10-2011-023991).

However, conventionally used Minoxidil or peptides consisting of the amino acid sequences of SEQ ID NO: 1 to SEQ ID NO: 3 still need to be improved in terms of preventing hair loss and improving hair growth promoting performance, reducing side effects, and increasing solubility in water.

To solve these problems, the inventors of the present invention have prepared Minoxidil-Nokkin, Minoxidil-Keramin 2 and Minoxidil-WINT peptides by chemically conjugating Minoxidil to the peptides consisting of the amino acid sequences of SEQ ID NO: 1 to SEQ ID NO: 3, respectively and have confirmed that the compounds promote the activity of the vascular endothelial growth factor associated with hair growth, promote the WINT pathway, and inhibit the activity of proteins involved in hair loss in the major BMP pathway, thereby completing the present invention.

DISCLOSURE

Technical Problem

The present invention is to solve the problems of the conventional hair growth solution, and thus it is a technical object of the present invention to provide a material having superior physiological properties such as stability to water while having the same or superior hair loss prevention and/or hair growth promoting function, as compared to the conventional hair growth solutions such as natural growth factors, peptides consisting of amino acid sequences of SEQ ID NO: 1 to SEQ ID NO: 3, or the Minoxidil.

Technical Solution

In order to achieve the above object, the present invention provides a compound having a structure in which the Minoxidil and peptide are chemically bonded.

According to one embodiment of the present invention, the peptide may be composed of 2 to 30, preferably 5 to 20, more preferably 8 to 15, and more preferably 10 to 12 amino acid sequences, but is not limited thereto.

According to another embodiment of the present invention, the peptide is preferably a water-soluble peptide, but is not limited thereto. According to a preferred embodiment of the present invention, the water-soluble peptide has preferably the ratio of hydrophilic side chain-containing amino acids of no less than 50%, preferably no less than 60%, more preferably no less than 70%, more preferably no less than 80%, more preferably no less than 90% and most preferably 100%. According to another preferred embodiment of the present invention, the water-soluble peptide has preferably no more than 5 amino acids, preferably no more than 4 amino acids, more preferably no more than 3 amino acids, more preferably no more than 2 amino acids, more preferably no more than 1 amino acid, which have hydrophilic side chains, and most preferably has no amino acid.

According to another embodiment of the present invention, the peptide may be, but is not limited to, a Nokkin peptide consisting of the amino acid sequence of SEQ ID NO: 1; a Keramin2 peptide consisting of the amino acid sequence of SEQ ID NO: 2; or a WINT peptide consisting of the amino acid sequence of SEQ ID NO: 3.

In addition, the present invention provides a pharmaceutical composition for hair loss prevention or hair growth promotion comprising any one of the compounds disclosed above.

In addition, the present invention provides a cosmetic composition for hair loss prevention or hair growth promotion comprising any one of the compounds disclosed above.

According to one embodiment of the present invention, the cosmetic composition may be, but is not limited to, formulations such as emollient beauty wash, nutrition beauty wash, nutrition creams, massage creams, essences, eye creams, cleansing creams, cleansing foams, cleansing water, packs, spray, powders, hair tonic, hair creams, hair lotions, hair shampoo, hair rinses, hair conditioners, hair spray, hair air-sol, pomades, sol-gel, emulsions, oils, waxes, or air-sol.

Advantageous Effects

The compounds according to the present invention, which have the structure in which the Minoxidil and the peptide are chemically bonded, have excellent physiological activity such as improvement of hair loss, hair growth promotion and cell growth promotion, and also has excellent stability in water and skin permeation rate, and thus can be useful as a composition for hair loss reduction and hair growth promotion.

However, the effects of the present invention are not limited to the above-mentioned effects, and other effects not mentioned can be clearly understood by those skilled in the art from the following description.

BEST MODE

Figure 1:
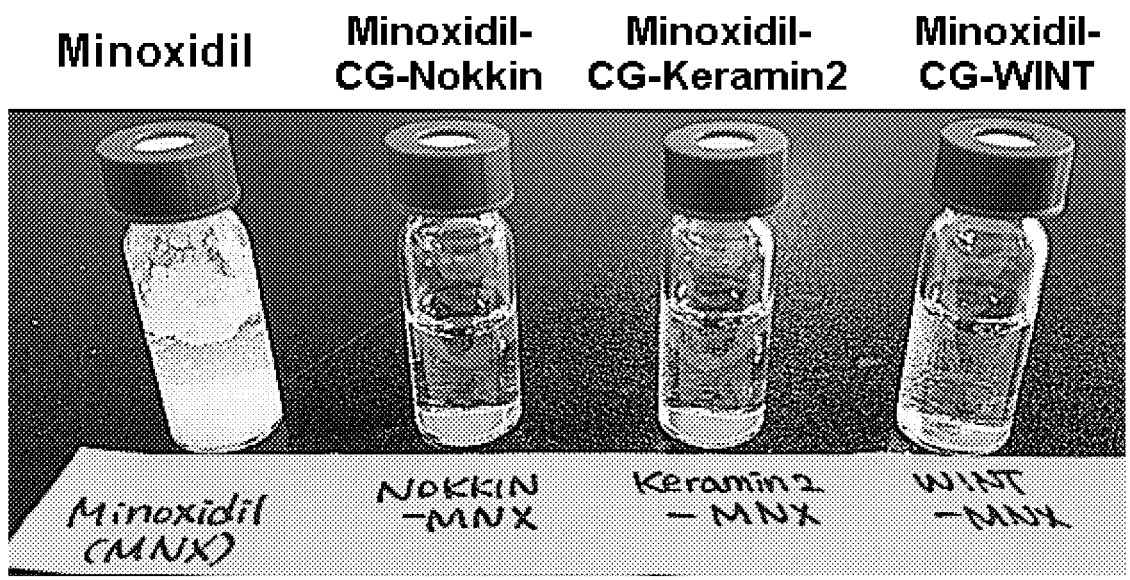
FIG. 1 is a photograph showing the solubility in water of the compound of the present invention and the Minoxidil.

In order to achieve the above object, the present invention provides a compound having a structure in which the Minoxidil and peptide are chemically bonded.

The Minoxidil is 6-amino-1,2-dihydro-1-hydroxy-2-imino-4-phenoxypyrimidine having a structure represented by the following formula 1:

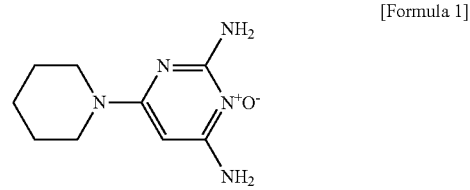

[Formula 1]

Hereinafter, the present invention will be described in detail.

The term "peptide" as used herein refers to a linear molecule formed by amino acid residues joined together by a peptide bond. The peptide can be prepared according to conventional biological or chemical synthesis methods known in the art, particularly solid-phase synthesis techniques (Merrifield, *J. Amer. Chem. Soc.,* 85:2149-54 (1963)).

The peptide is intended to increase the water solubility of the Minoxidil. In this respect, the peptide is preferably a water-soluble peptide, but is not limited thereto. According to one embodiment of the present invention, the peptide is composed of 2 to 30, preferably 5 to 20, more preferably 8 to 15, and more preferably 10 to 12 amino acid sequences. According to a preferred embodiment of the present invention, the peptide has preferably the ratio of hydrophilic side chain-containing amino acids of no less than 50%, preferably no less than 60%, more preferably no less than 70%, more preferably no less than 80%, more preferably no less than 90% and most preferably 100%. On the other hand, the peptide has the ratio of hydrophobic side chain-containing amino acid of less than 50%, preferably no more than 40%, more preferably no more than 30%, more preferably no more than 20%, more preferably no more than 10% and most preferably 0%. The term "hydrophilic side chain-containing amino acid" as used herein refers to arginine (Arg), histidine (His), lysine (Lys), asparaginic acid (Asp), glutamic acid (Glu), serine (Ser), threonine (Thr), asparagine (Asn), glutamine (Gln), cysteine (Cys), selenocysteine (Sec), glycine (Gly) and proline (Pro) and the term "hydrophobic side chain-containing amino acid" refers to alanine (Ala), valine (Val), isoleucine (Ile), leucine (Leu), methionine (Met), phenylalanine (Phe), tyrosine (Tyr) and tryptophan(Trp), but is not limited thereto, and in addition to the above-mentioned amino acids present in nature, modified products thereof and the like can be also used without limitation. According to a preferred embodiment of the present invention, the hydrophobic side chain-containing amino acid is present in the peptide in an amount of not more than 5, preferably not more than 4, more preferably not more than 3, more preferably not more than 2, more preferably not more than 1, and most preferably 0. According to one embodiment of the present invention, the peptide is preferable, but is not limited to, a Nokkin peptide consisting of the amino acid sequence of SEQ ID NO: 1; a Keramin2 peptide consisting of the amino acid sequence of SEQ ID NO: 2; and a WINT peptide consisting of the amino acid sequence of SEQ ID NO: 3.

According to one embodiment of the present invention, the compound of the present invention has cell growth promoting ability with regard to human umbilical vein endothelial cells (HUVEC) and human hair dermal papilla cells (HHDPC). According to another embodiment of the present invention, the compound of the present invention has a function of activating the WNT signal transduction pathway. According to another embodiment of the present invention, the compound of the present invention transfers the β-catenin into the nucleus. According to another embodiment of the present invention, the compound of the present invention blocks the BMP signal pathway, which is a major factor of hair loss.

The compound of the present invention has excellent stability by itself, but the stability can be further improved by modifying any amino acid constituting the peptide bound to the compound. According to one embodiment of the present invention, the N-terminal of the peptide can bind with a protecting group selected from the group consisting of acetyl group, fluorenyl methoxy carbonyl group, formyl group, palmitoyl group, myristyl group, stearyl group and polyethylene glycol (PEG), and thus the stability can be further improved. According to another embodiment of the present invention, the peptide can bind with a protecting group selected from the group consisting of acetyl group, fluorenyl methoxy carbonyl group, formyl group, palmitoyl group, myristyl group, stearyl group and polyethylene glycol (PEG), and thus the stability can be further improved.

Modifications of the amino acids as described above play a role in greatly improving the stability of the compounds of the present invention. The term "stability" as used herein is intended to encompass "in vitro" stability as well as "in vivo" stability such as storage stability (e.g., room temperature storage stability). In addition, the above-mentioned protecting group plays a role of protecting the compound of the present invention from attack of protease in vivo and in vitro.

In addition, the present invention provides a composition for treating or ameliorating hair loss comprising the compound as an effective component. According to another embodiment of the present invention, the present invention provides a composition for improving skin condition comprising the peptide as an effective component. In the present invention, the composition may be in the form of a pharmaceutical composition or health food, but is not limited thereto.

Since the composition of the present invention comprises the aforementioned compound of the present invention as an effective component, the contents common to both of them are omitted in order to avoid the excessive complexity of the present specification.

According to one embodiment of the present invention, the treatment or amelioration of hair loss by the compounds of the present invention is hair growth promotion or hair production. According to a preferred embodiment of the present invention, the compound of the present invention has HUVEC and HHDPC cell growth promotion ability, and promotes the β-catenin signal transduction pathway, a typical signal transduction pathway of WINT protein. According to another embodiment of the present invention, the compound of the present invention blocks the BMP signal pathway, which is a major factor of hair loss. Animal experiments based on these results showed that the compound of the present invention significantly promoted hair growth. Therefore, the composition of the present invention is very effective in improving hair growth and skin condition.

Also, according to one embodiment of the present invention, the improvements in skin condition by the compound of the present invention are improvement in wrinkles, improvement in skin elasticity, prevention of skin aging, improvement in skin moisturizing, treatment of wounds, or skin regeneration.

Since the composition of the present invention comprises the aforementioned compound of the present invention as an effective component, the content common to both of them is omitted in order to avoid the excessive complexity of the present specification.

According to a preferred embodiment of the present invention, the composition of the present invention is a pharmaceutical composition comprising (a) a pharmaceutically effective amount of the aforementioned compound of the present invention and (b) a pharmaceutically acceptable carrier.

The term "pharmaceutically effective amount" as used herein refers to an amount sufficient to achieve efficacy or activity of the compound of the present invention described above.

The pharmaceutically acceptable carriers contained in the pharmaceutical composition of the present invention include those conventionally used in the preparation of formulations, and include for example, but is not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oils and the like. The pharmaceutical composition of the present invention may further include lubricants, wetting agents, sweetening agents, flavoring agents, emulsifying agent, suspending agents, preservatives and the like in addition to the above components. Suitable pharmaceutically acceptable carriers and formulations are described in detail in Korean Laid-open Patent Publication No. 2017-0027312.

The pharmaceutical composition of the present invention can be prepared by formulating as a unit dosage form or by inserting into a multi-dose container using pharmaceutically acceptable carriers and/or excipients, according to a method which can be easily carried out by a person having ordinary skill in the art to which the present invention pertains. In this case, the formulations may be in the form of solutions, suspensions or emulsions in oil or aqueous media, or may be in the form of extracts, powders, granules, tablets, capsules or gels (e.g., hydrogels), and may additionally include dispersing agents or stabilizers.

The pharmaceutical composition according to the present invention can be administered orally or parenterally at the time of clinical administration and can be used in the form of a general pharmaceutical preparation. That is, the pharmaceutical composition of the present invention can be administered orally or parenterally as various clinical formulations at the time of actually clinical administration, and when the pharmaceutical composition of the present invention is formulated, it is prepared using diluents or excipients such as fillers, extenders, binders, wetting agents, disintegrating agents, and surfactants which are usually used. Solid formations for oral administration may include tablets, pills, powders, granules or capsules, and the solid formations may be prepared by mixing a herbal extract or a fermented herbal extract with one or more excipients such as starch, calcium carbonate, sucrose, lactose or gelatin. In addition to the simple excipients, lubricants such as magnesium stearate and talc are also used. Liquid formations for oral administration, comprising suspension, liquid for internal use, emulsion, syrup, etc., may include simple diluents such as water or liquid paraffin, as well as various excipients such as wetting agents, sweeting agents, fragrance, or preservatives. Formulations for parenteral administration may include sterilized aqueous solution, nonaqueous solvent, suspending agent, emulsion, freeze drying agent or suppository. Nonaqueous solution and suspension may be Nonaqueous solution and suspension may be propylene glycol, polyethylene glycol, vegetable oil such as olive oil, ester available for injection such as ethyl oleate. The base of suppository may be WITEPSOL®, macrogol, TWEEN® 61, cacao oil, laurin oil, glycerol, gelatin and the like.

Dosage units may contain, for example, 1, 2, 3 or 4 times, or ½, ⅓ or ¼ times the individual dosage. Individual dosage will contain the amount of the active drug which is administered in a single dose, and usually correspond to all, one-half, one-third, or one-fourth of the daily dose.

The pharmaceutical composition of the present invention can be prepared by formulating as a unit dosage form or by inserting into a multi-dose container using pharmaceutically acceptable carriers and/or excipients, according to a method which can be easily carried out by a person having ordinary skill in the art to which the present invention pertains. In this case, the formulations may be in the form of solutions, suspensions or emulsions in oil or aqueous media, or may be in the form of extracts, powders, granules, tablets, capsules or gels (e.g., hydrogels), and may additionally include dispersing agents or stabilizers.

According to a preferred embodiment of the present invention, the composition of the present invention is a cosmetic composition comprising (a) a cosmetically effective amount of the compound of the present invention as described above; and (b) a cosmetically acceptable carrier.

The term "cosmetically effective amount" as used herein refers to the amount of the composition of the present invention described above sufficient to achieve a skin condition-improving effect.

The cosmetic compositions of the present invention may be prepared as any formulation conventionally produced in the art, for example, including solutions, suspensions, emulsions, pastes, gels, creams, lotions, powders, soaps, surfactant-containing cleansing, oils, powder foundations, emulsion foundations, wax foundations and sprays, but are not limited thereto. More specifically, the cosmetic compositions of the present invention may be prepared in various forms, for example, solutions, sol-gels, emulsions, oils, waxes, air-sols and the like, such as emollient beauty wash, nutrition beauty wash, nutrition creams, massage creams, essences, eye creams, cleansing creams, cleansing foams, cleansing water, packs, sprays, powders, hair tonic, hair creams, hair lotions, hair shampoo, hair rinses, hair conditioners, hair-sprays, hair air-sols, pomades, and gels, but are not limited thereto.

The paste, cream or gel formulations of the present invention may include animal oils, plant oils, waxes, paraffin, starch, tragacanth, cellulose derivates, polyethylene glycol, silicon, bentonite, silica, talc or zinc oxide as a carrier component.

The powder or spray formulations of the present invention may include lactose, talc, silica, aluminum hydroxide, calcium silicate or polyamide powder as a carrier component, and especially, the spray formulation may additionally include, but is not limited to, propellants such as chlorofluorohydrocarbon, propane/butane or dimethyl ether.

The solution or emulsion formulations of the present invention may include, but are not limited to, solvents, solubilizing agents or emulsifying agents as a carrier component, such as water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

The suspension formulation of the present invention may include, but is not limited to, diluting agents in liquid phase, such as water, ethanol and propylene glycol, suspending agents such as ethoxylated isostearyl alcohol, polyoxyethylene sorbitol ester and polyoxyethylene sorbitan ester, microcrystalline cellulose, aluminum metal hydroxide, bentonite, agar and tragacanth, as a carrier component.

If the formulation of the present invention is the surfactant-containing cleansing, the formulation may include aliphatic alcohol sulfate, aliphatic alcohol ether sulfate, sulfosuccinic acid monoester, isethionate, imidazolium derivates, methyl taurate, sarcosinate, fatty acid amide ether sulfate, alkylamidobetaine, aliphatic alcohols, fatty acid glyceride, fatty acid diethanolamide, plant oils, lanolin derivates or ethoxylated glycerol fatty acid ester as a carrier component, but is not limited thereto.

If the formulation of the present invention is a hair shampoo, base components for forming the hair shampoo, such as thickeners, surfactants, viscosity adjusting agents, moisturizers, pH adjusting agents, antiseptics, essential oils, etc. are mixed with the compound of the present invention. CDE can be used as a thickener, the surfactant may be LES which is an anionic surfactant and cocobetaine which is an amphoteric surfactant, the viscosity adjusting agent may be Polyquater, the moisturizer may be glycerin, the pH adjusting agent may be citric acid or sodium hydroxide, and the preservative may be a grapefruit extract. In addition, essential oils such as cedarwood, peppermint, and rosemary, and silk amino acid, pentanol, and vitamin E can be added. According to one embodiment of the present invention, the hair shampoo may comprise, but is not limited to, 5 to 10 parts by weight of CDE, 30 to 40 parts by weight of LES, 10 to 20 parts by weight of cocobetaine, 0.1 to 0.2 parts by weight of Polyquater, 5 to 10 parts by weight of glycerin, 0.1 to 1.01 part by weight of grapefruit extract, 0.5 to 1 part by weight of silk amino acid, 0.5 to 1 part by weight of pentanol, 0.5 to 2 parts by weight of vitamin E, and 0.01 to 0.1 part by weight of any one of cedarwood, peppermint and rosemary as an essential oil, on the basis of 100 parts by weight of the compound of the present invention.

The components included in the cosmetic composition of the present invention may include, in addition to the compound of the present invention as an effective component and carrier components, components commonly used in cosmetic compositions and may include, but are not limited to, conventional adjuvants such as antioxidants, stabilizers, solubilizers, vitamins, pigments, and perfumes.

In addition, the present invention provides a method for hair loss prevention or hair growth promotion comprising the step of transdermally administering the compound to the affected part of a subject suffering from hair loss.

The percutaneous administration may be, but not limited to, topical spreading or injection.

The affected part may include, but is not limited to, at least one selected from the group consisting of scalp, face, beard, head, mustache, body, eyebrows and eyelid part.

The subject suffering from hair loss may be a patient suffering from any one hair loss disorder selected from the group consisting of androgen alopecia, areata alopecia, systemic alopecia, degenerative alopecia, trichotillomania, telogen alopecia, anagen effluvium, alopecia cicatrisata, cicatricial alopecia, thin scalp, hair shaft dystrophy, infectious hair diseases, genetic diseases and chemotherapy, hormone imbalance, mycotic infection, and alopecia by drug ingestion.

Hereinafter, the present invention will be described in detail with reference to Examples and Experimental Examples.

However, the following Examples and Experimental Examples are provided only for illustrating the present invention, and the content of the present invention is not limited by the following Examples and Experimental Examples.

<Example 1> Synthesis and Solubility Evaluation of Compound of the Present Invention <1-1> Synthesis of Peptide
<1-1-1> Synthesis of Peptide of SEQ ID NO: 3

700 mg of chlorotrityl chloride resin (CTL resin, Nova biochem [0064] Cat No. 01-64-0021) was placed in a reaction vessel, and 10 ml of methylene chloride (MC) was added thereto, followed by stirring for 3 minutes. The solution was removed, and 10 ml of dimethyl formamide (DMF) was added thereto. After stirring for 3 minutes, the solvent was removed again. 10 ml of dichloromethane solution was added to the reactor, and after adding 200 mmol of Fmoc-Cys(trt)-OH (Bachem, Swiss) and 400 mmol of diisopropylethylamine (DIEA) were added, stirred and thus dissolved well, and reacted with stirring for 1 hour. After the reaction, washing was performed, and methanol and DIEA (2:1) were dissolved in dichloromethane (DCM), reacted for 10 minutes, and washed with excess DCM/DMF (1:1). The solution was removed, and 10 ml of dimethyl formamide (DMF) was added thereto. After stirring for 3 minutes, the solvent was removed again. 10 ml of the deprotection solution (20% piperidine/DMF) was added to the reaction vessel, stirred for 10 minutes at room temperature, and then the solution was removed. The same amount of the deprotection solution was added, and the reaction was maintained for 10 minutes. Then, the solution was removed, and washed twice with DMF, once with MC and once with DMF for 3 minutes each to obtain the Cys(trt)-CTL resin.

To the new reactor, 10 ml of DMF solution was added, 200 mmol of Fmoc-His(trt)-OH (Bachem, Swiss), 200 mmol of HoBt and 200 mmol of Bop were added, stirred and dissolved well. 400 mmol of DIEA was added to the reactor in two portions and then stirred for at least 5 minutes until all solids dissolved. The dissolved amino acid mixture solution was placed in the reaction vessel containing the deprotected resin and allowed to react for 1 hour at room temperature with stirring. The reaction solution was removed, and stirred with DMF solution three times for 5 minutes each, and then removed. A small amount of the reaction resin was taken and the degree of reaction was checked using a Kaiser test (Nihydrin Test). His(trt)-Cys(trt)-CTL resin was prepared by deprotecting twice in the same manner as described above while using the deprotection solution. After thoroughly washing with DMF and MC and performing a Kaiser test once again, the following amino acid adhesion experiment was performed as described above.

Based on the selected amino acid sequence, chain reactions were performed in the order of Fmoc-Cys(trt), Fmoc-Arg, Fmoc-Gln(trt), Fmoc-Val, Fmoc-Arg, Fmoc-Thr, Fmoc-Gln(trt) and Fmoc-Arg(pbf). The Fmoc-protecting group was removed by reacting with the deprotection solution twice for 10 min and then washing well. Acetic anhydride, DIEA and HoBt were added and acetylation was carried out for 1 hour, and then the peptidyl resin thus prepared was washed three times each with DMF, MC and methanol. The nitrogen was slowly flowed and dried, and then thoroughly dried by reducing the pressure under vacuum under $P_2O_5$. Thereafter, after adding 30 ml of leaving solution [95% of trifluoroacetic acid, 2.5% of distilled water, 2.5% of thioanisole], the reaction was maintained for 2 hours with occasional shaking at room temperature. The resin was filtered and the resin was washed with a small amount of TFA solution and then combined with the mother liquor. Distillation was carried out using reduced pressure so that the total volume remained about half, and 50 ml of cold ether was added to induce precipitation. The precipitates were collected by centrifugation and washed with cold ether two times. The mother liquor was removed and sufficiently dried under nitrogen to obtain 0.65 g of crude $NH_2$-Arg-Gln-Thr-Arg-Val-Gln-Arg-Cys-His-Cys-OH peptide (SEQ ID NO: 3) (Yield: 92.6%). A molecular weight of 1287.1 (theoretical value: 1286.5) was obtained when measured by using a molecular weight analyzer.

<1-1-2> Synthesis of Peptides of SEQ ID NO: 1 and SEQ ID NO: 2

The peptide (Glu-Leu-Ile-Glu-His-Gly-Gly-Gly-Arg-Pro-Ala-Asp: ELIEHGGGRPAD) of SEQ ID NO: 1 and the peptide (Ac-Tyr-Lys-Ser-Lys-Lys-Gly-Gly-Trp-Thr-His: Ac-YKSKKGGWTH) of SEQ ID NO: 2 were synthesized using the same method as the example <1-1-1>.

TABLE 1

| SEQ ID NO | Amino acid sequence | Analytical value (mass spectrometer) | |
|---|---|---|---|
| | | Analytical value | Theoretical value |
| 1 | ELIEHGGGRPAD | 1250.9 | 1250.35 |
| 2 | Ac-YKSKKGGWTH | 1233.8 | 1233.4 |
| 3 | RQTRVERCHC | 1287.1 | 1286.5 |

<1-2> Synthesis of Compound of the Present Invention

The peptidyl resin (1 mmol) and 3.9 g (3 mmol, 3.0 equiv.) of N,N'-diisopropylethylamine (DIPEA) in a peptide reactor were dissolved in 10 mL of 1-methyl-2-pyrrolidinone (NMP), and then, 200 mg (2 mmol, 2.0 equiv.) of succinic anhydride was added and reacted at room temperature for 2 hours. The solvent was filtered off and washed with fresh NMP (5 mL×2) to obtain a peptidyl resin-succinic acid conjugate. 270 mg (0.2 mmol, 2.0 equiv.) of 1-hydroxybenzotriazole (HOBt) and 759 mg (0.2 mmol, 2.0 equiv.) of N,N,N',N'-tetramethyl-O-(1H-benzotriazol-1-yl) uronium hexafluorophosphate (HBTU) were dissolved in 10 mL of dimethyl sulfoxide (DMSO) and reacted for 30 minutes. 388 mg (0.3 mmol, 3 equiv.) of N,N-diisopropylethylamine (DIPEA), 41.8 mg (0.2 mM) of Minoxidil analogue and peptidyl resin-succinic acid conjugate (0.1 mmol) were added and reacted at room temperature for 72 hours, and filtered to obtain the reacted peptidyl resin. The obtained resin was reacted with cleavage solution at room temperature for 2 hours to remove the resin and protecting group, and crystallized using 10 mL (10 mmol) of diethyl ether to obtain a Minoxidil hybrid peptide.

[Reaction Scheme 1] Reaction scheme of conjugate of Minoxidil and peptide

[Reaction Scheme 2] Reaction scheme of Minoxidil-Nokkin conjugate

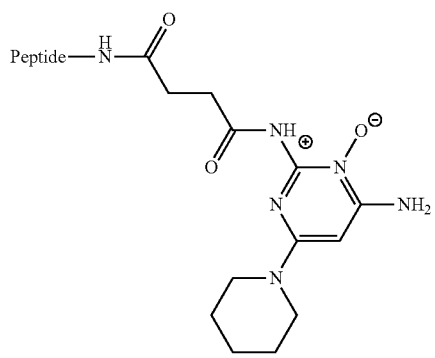
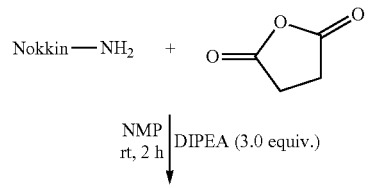
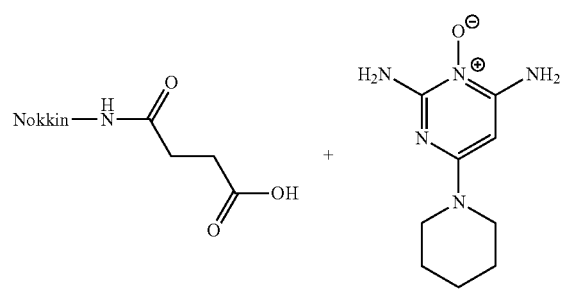
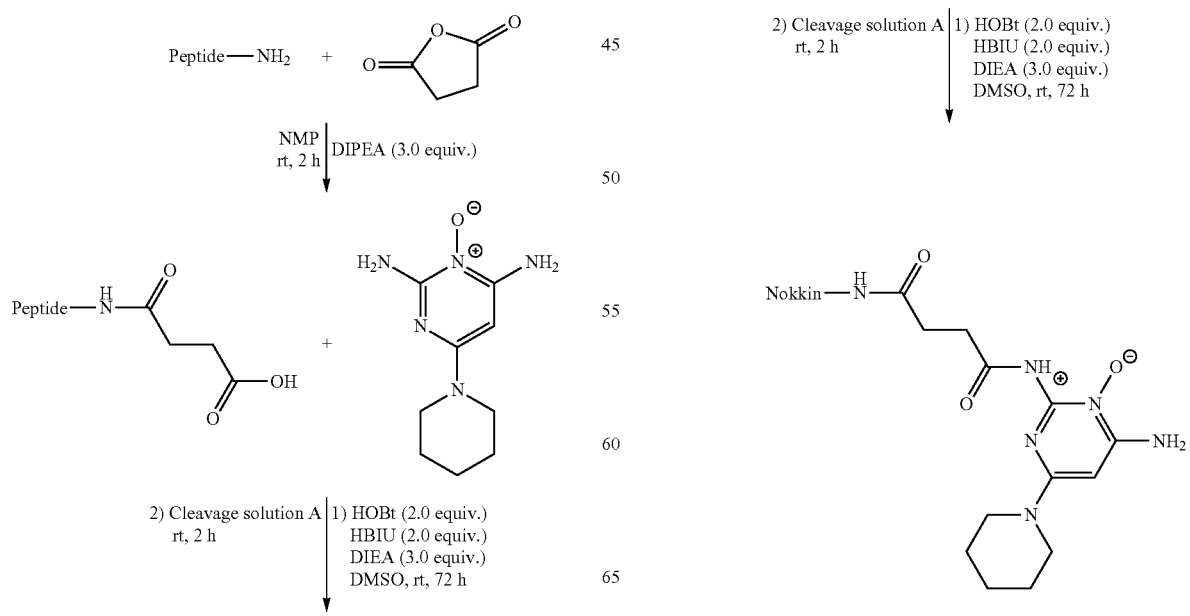
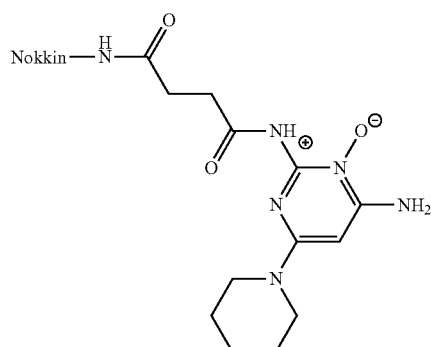

[Reaction Scheme 3] Reaction scheme of Minoxidil-Keramin2 conjugate

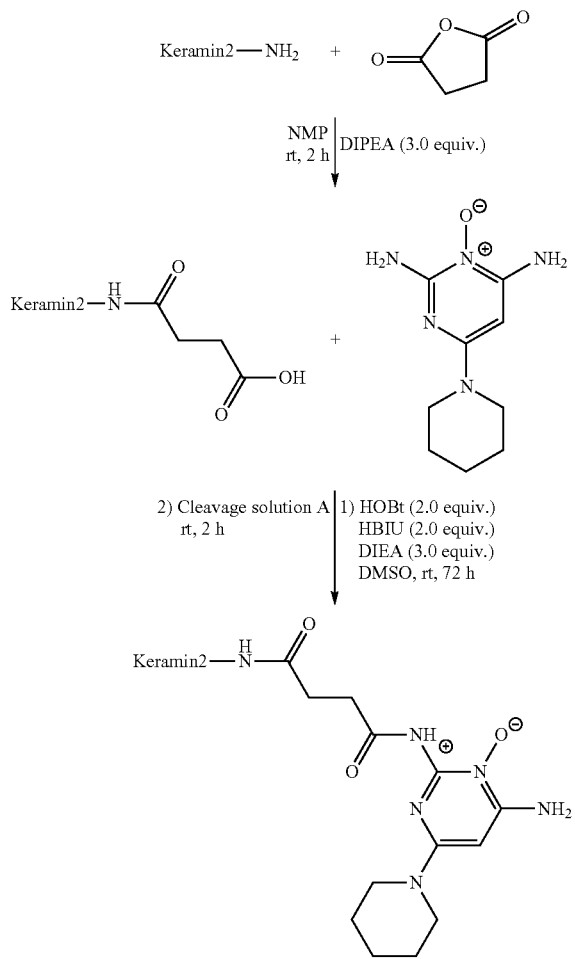

[Reaction Scheme 4] Reaction scheme of Minoxidil-WINT conjugate

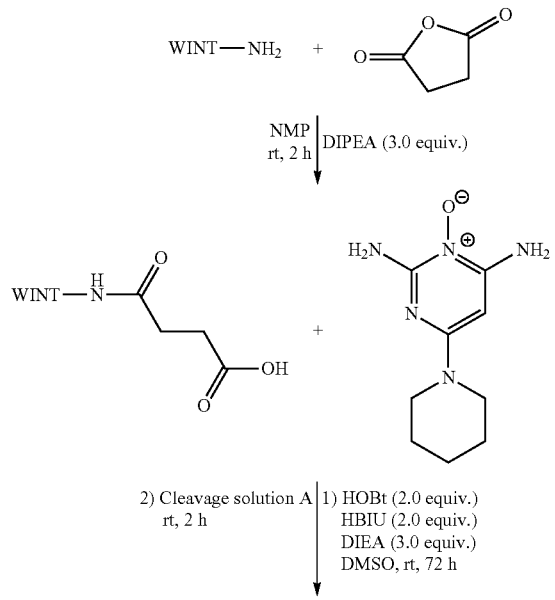

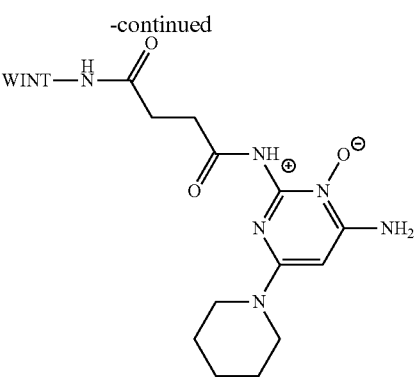

<1-3> Evaluation of Solubility

The Minoxidil-CG-Nokkin, the Minoxidil-CG-Keramin2, and the Minoxidil-CG-WINT prepared in Example 1-1 were dissolved in DW at a concentration of 10 mg/ml, respectively. The Minoxidil was used as a control.

As a result, it was confirmed that the Minoxidil was almost insoluble in water at the same concentration and thus was in opaque state, whereas all of the three compounds of the present invention were completely dissolved in water (see FIG. 1).

<Example 2> Evaluation of the Degree of Cell Proliferation Upon Treatment of the Compound of the Present Invention <2-1> Evaluation of Cell Proliferation for Human Umbilical Vein Endothelial Cell (HUVEC)

In order to confirm the function of the compound of the present invention synthesized in Example 1, HUVEC was treated with the compound of the present invention to confirm the degree of proliferation. 3000 HUVECs were placed in each well of a 96-well plate and incubated in a $CO_2$ incubator for 24 hours. After 24 hours, the medium was replaced with serum-free DMEM medium, and the three compounds of the present invention synthesized in Example 1 and Minoxidil were added at 0.5 uM, 5 uM, and 50 uM concentrations, respectively, to the cells, and incubated for 72 hours. After the incubation was completed, the incubation supernatant was removed, and the cells were fixed using ethanol and washed three times with PBS (phosphate buffer saline). After removing the washing solution, the cells were treated with a colorimetric SRB solution and washed thoroughly with 1% acetic acid. Thereafter, the cells were observed with a microscope to observe the viability of the cells. To the stained cells, 10 mM Trizma base (pH 10.5) solution were added to elute the SRB, and then the absorbance was measured by ultraviolet light of a wavelength of 560 nm to measure the viability of the cells.

Figure 2:
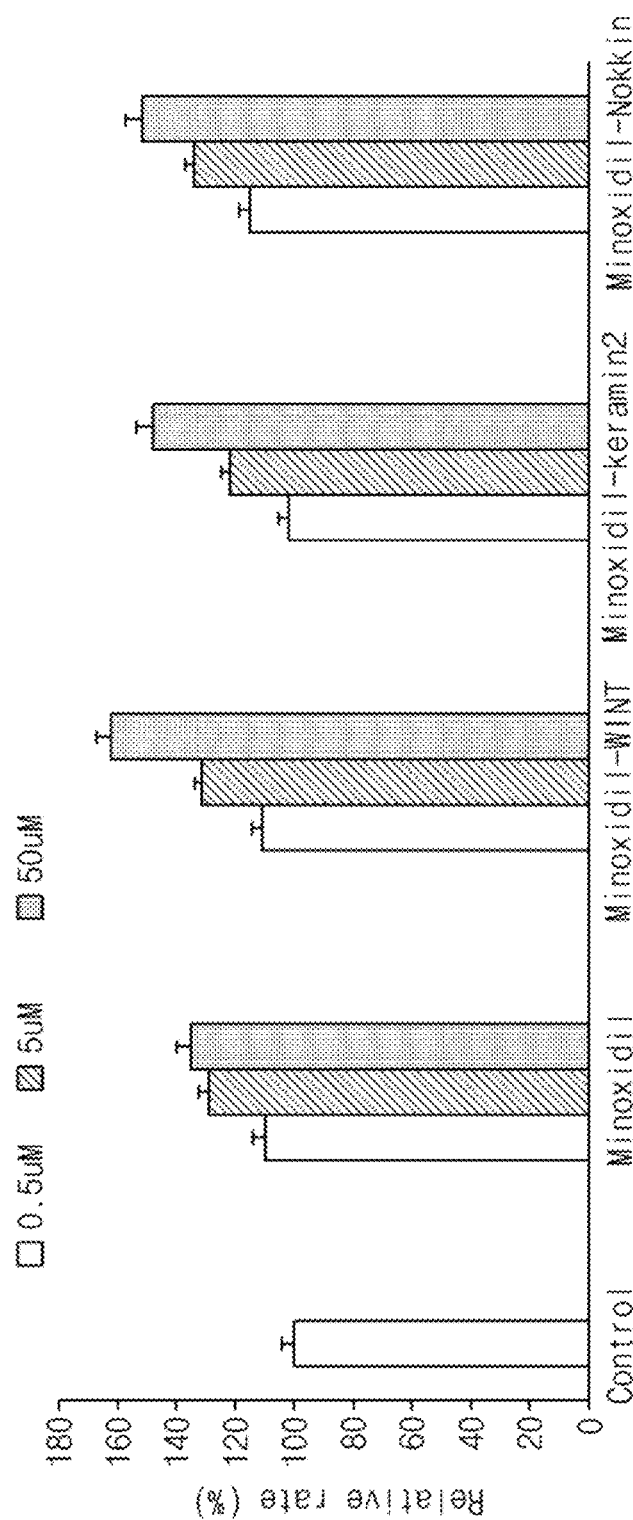
FIG. 2 is a graph showing the degree of cell proliferation of human umbilical vein endothelial cells (HUVEC) when treated with the compound of the present invention.

As a result, it was confirmed that in the case of the three compounds of the present invention at a low concentration, the cell proliferation was shown to be similar to that of the control group, the Minoxidil, but the degree of cell proliferation was markedly increased compared to the Minoxidil as the concentration was increased (see FIG. 2).

<2-2> Evaluation of Cell Proliferation for Human Hair Dermal Papilla Cells (HHDPC)

3000 HHDPCs were placed in each well of a 96-well plate and incubated in a $CO_2$ incubator for 24 hours. The medium was replaced with serum-free DMEM medium, and the three compounds of the present invention and Minoxidil were added at 0.5 uM, 5 uM, and 50 uM concentrations, respectively, and incubated for 72 hours. After completion of the incubation, cells were stained in the same manner as in Example 2-1, and SRB was eluted to quantify the degree of cell proliferation.

Figure 3:
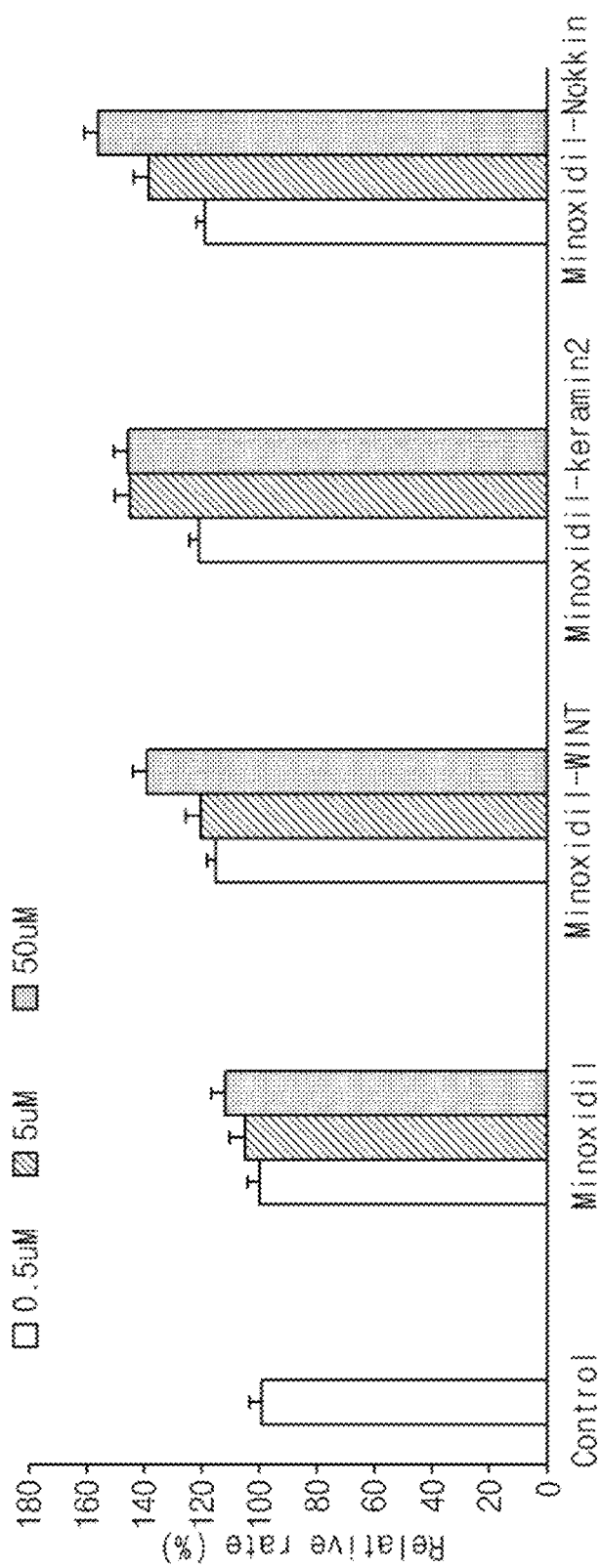
FIG. 3 is a graph showing the degree of cell proliferation of human hair dermal papilla cells (HHDPC) when treated with the compound of the present invention.

As a result, it was confirmed that the three compounds of the present invention have a higher degree of cell proliferation than the Minoxidil, and the degree of cell proliferation is significantly increased in proportion to the treatment concentration (see FIG. 3).

<Example 3> Evaluation of the Effect of the Compound of the Present Invention on the Expression of VEGF and TGFβ1

Since VEGF plays a role in angiogenesis and expansion function and TGFβ1 affects hair loss, the level of expression of VEGF and TGFβ1 was confirmed when treated with the compound of the present invention.

<3-1> Evaluation of mRNA Amount (Transcription Level)

VEGF was expressed by HUVECs and TGFβ1 was expressed by hair follicle dermal papilla cells. Two cells were placed in each 6-well plate at a rate of $1\times10^3$ cells/well. After 24 hours of incubation in a $CO_2$ incubator, the medium was replaced with serum-free DMEM medium. Three compounds of the present invention and Minoxidil were added to the cells at 5 uM and 50 uM concentration, respectively, and incubated for 24 hours. After incubated cells were harvested, RNA was extracted using an RNA extraction kit and RT-PCR was performed to confirm the degree of expression of VEGF and TGFβ1. The primers used in the RT-PCR are shown in table 2.

<3-2> Evaluation of the Amount of Protein (Translation Level)

HUVECs were placed in each well of a 6-well plate at $1\times10^3$ cells/well. Incubation was performed in a $CO_2$ incubator for 24 hours. After replacing the medium with serum-free DMEM medium, the three compounds of the present invention and the Minoxidil were added respectively to the cells at a concentration of 5 uM and 50 uM, and then incubated for 24 hours. Protein was extracted using protein extraction kit and Western blotting was performed. After preparing 12% SDS-PAGE, 15 ug of protein was loaded onto the prepared SDS-PAGE and transferred to PVDF membrane. Blocking was performed with 5% skim milk solution at room temperature for 1 hour. The primary antibody (anti-VEGF antibody, anti-alpha tubulin antibody) was attached at a concentration of 1/3000 at room temperature for 2 hours. Three washes were performed with PBST for 10 minutes, and the secondary antibody was attached at a concentration of 1/5000 at room temperature for 1 hour. After washing three times for 15 minutes with BST, the detection was performed.

Figure 7:
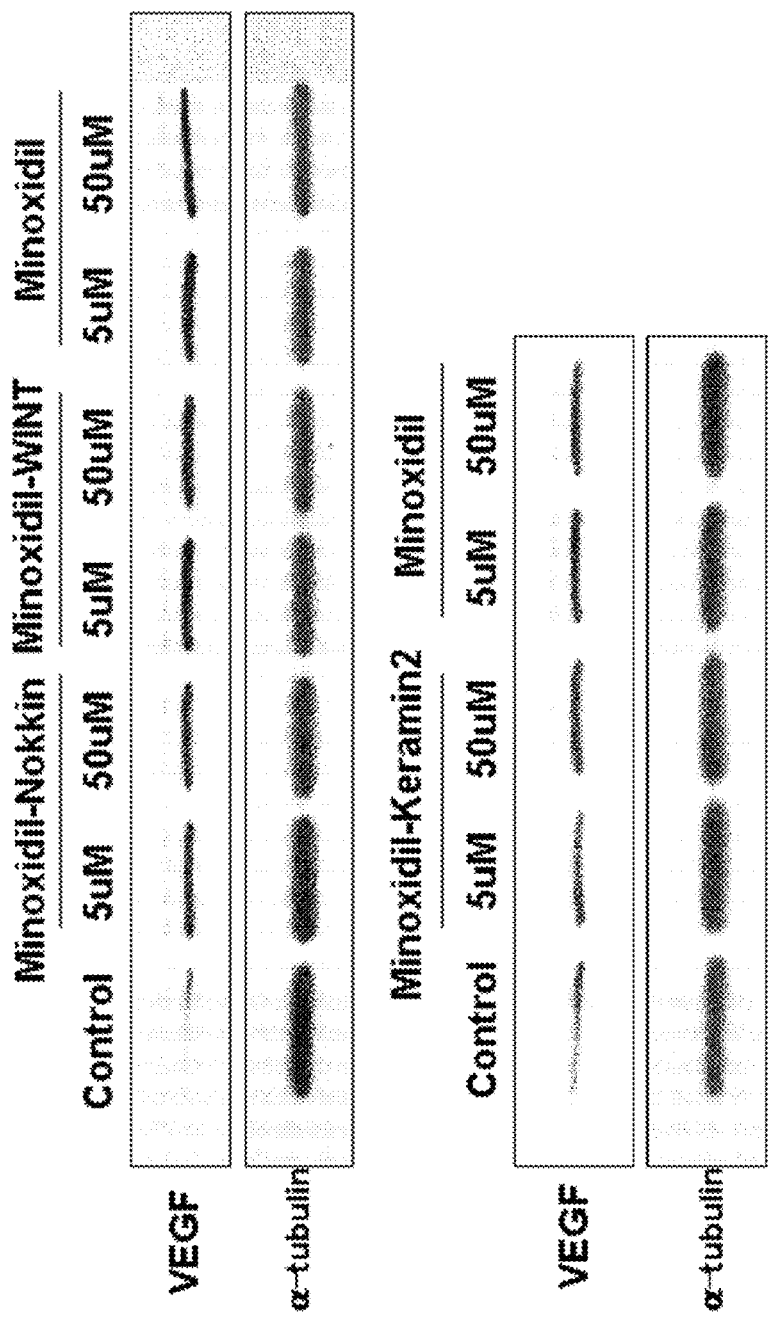
FIG. 7 shows the result of confirming the amount of VEGF protein when treated with the compound of the present invention.

As a result, it was found that the three compounds of the present invention are similar to the Minoxidil or have a higher than the Minoxidil with regard to the expression level of VEGF (see FIG. 7). Since the three compounds of the present invention increase the expression of VEGF that plays a role in angiogenesis and expansion function, the compounds of the present invention can be useful for hair loss prevention or improvement.

TABLE 2

| Kind of primer | Sequence | SEQ ID NO |
|---|---|---|
| VEGF Forward | (5') CCATGAACTTTCTGCTGTCTT (3') | 4 |
| VEGF Reverse | (5') TCGATCGTTCTGTATCAGTCT (3') | 5 |
| TGFβ1 Forward | (5') GCCCTGGATACCAACTATTGC (3') | 6 |
| TGFβ1 Reverse | (5') TCAGCACTTGCAGGAGTAGCG (3') | 7 |
| GAPDH Forward | (5') GGAGCCAAAAGGGTCATCAT (3') | 8 |
| GAPDH Reverse | (5') GTGATGGCATGGACTGTGGT (3') | 9 |

Figure 4:
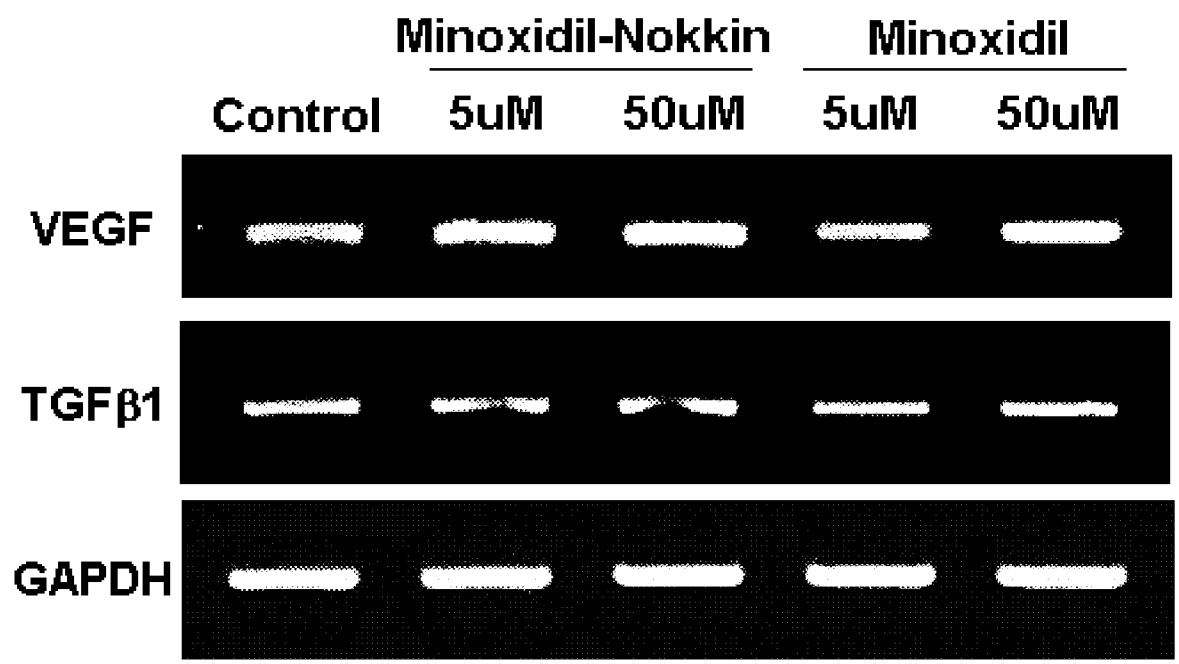
FIG. 4 shows the results of confirming the amount of 5 mRNA of VEGF and TGFβ1 when treated with the Minoxidil-Nokkin conjugate of the present invention.
Figure 5:
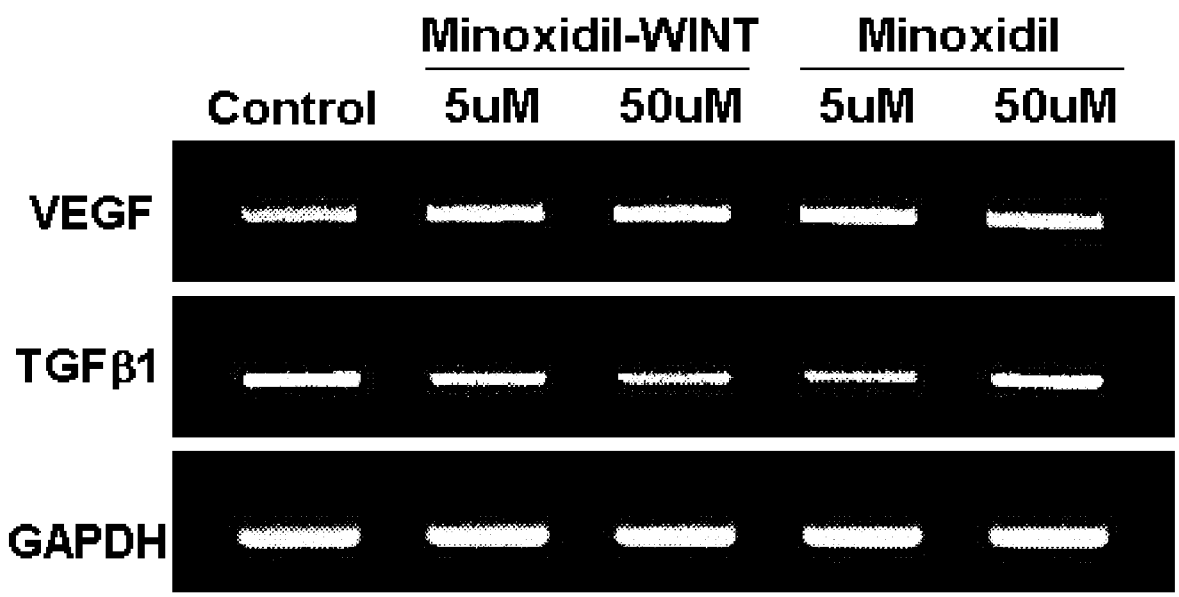
FIG. 5 shows the results of confirming the amount of 5 mRNA of VEGF and TGFβ1 when treated with the Minoxidil-WINT conjugate of the present invention.
Figure 6:
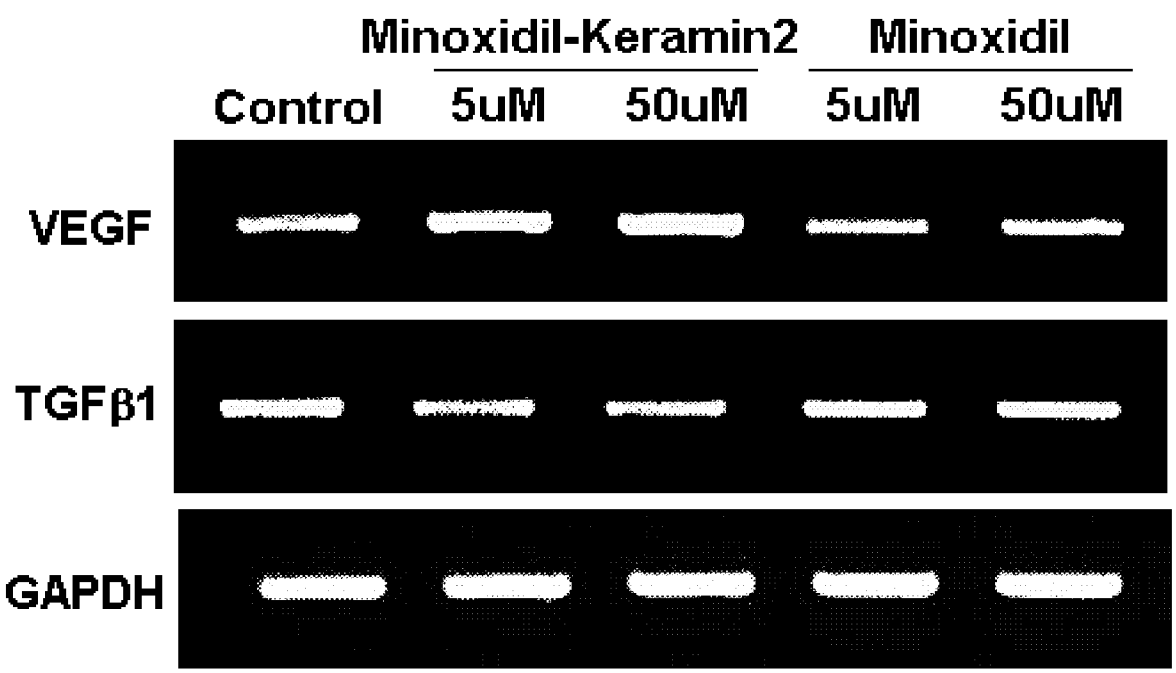
FIG. 6 shows the results of confirming the amount of 5 mRNA of VEGF and TGFβ1 when treated with the Minoxidil-Keramin 2 conjugate of the present invention.

As a result, the three compounds of the present invention showed a higher expression of VEGF than that of the Minoxidil, and especially VEGF expressions in the case of the Minoxidil-Nokkin and the Minoxidil-Keramin2 were significantly higher than that of Minoxidil (see FIGS. 4 to 6). In addition, the expressions of TGFβ1 in the case of the three compounds of the present invention were lower than that of the Minoxidil, and in particular, the expression level of TGFβ1 in the case of the Minoxidil-Nokkin was significantly lower than that of the Minoxidil at the same concentration (see FIGS. 4 to 6). From these results, it can be seen that since the three compounds of the present invention have a high expression amount of VEGF that plays a role in angiogenesis and expansion function and have a low expression amount of TGFβ1 that is involved in hair loss, the three compounds of the present invention can be used for hair loss prevention or improvement.

<Example 4> Evaluation of the Degree of Angiogenesis of the Compound of the Present Invention 200 μl of Matrigel was placed in each well of a 24-well plate and incubated for 1 hour. $1\times10^5$ HUVECs were placed in each Matrigel. Three compounds of the present invention and Minoxidil were added to the cell-seeded Matrigel at a concentration of 5 uM and 50 uM, respectively. VEGF used as a positive control was treated at a concentration of 50 nM and 100 nM. After 6 hours, the degree of angiogenesis of HUVEC was observed through a microscope.

Figure 8:
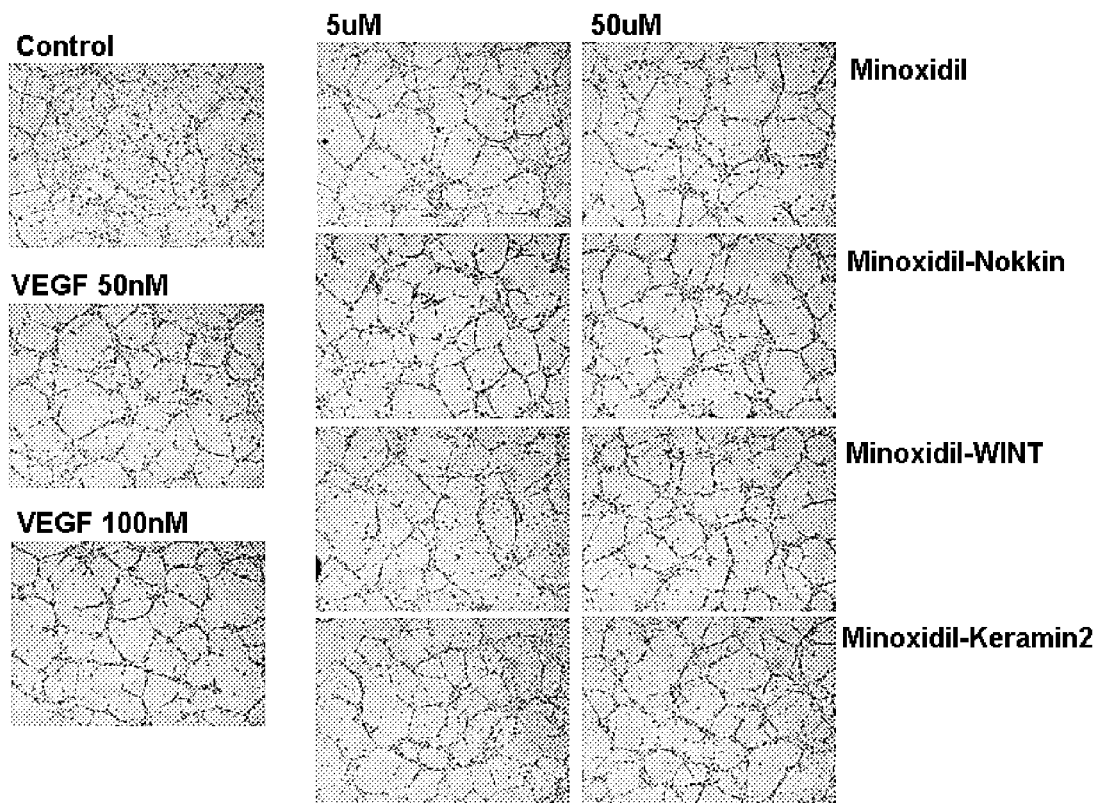
FIG. 8 shows the degree of blood vessel formation when treated with the compounds of the present invention.
Figure 9:
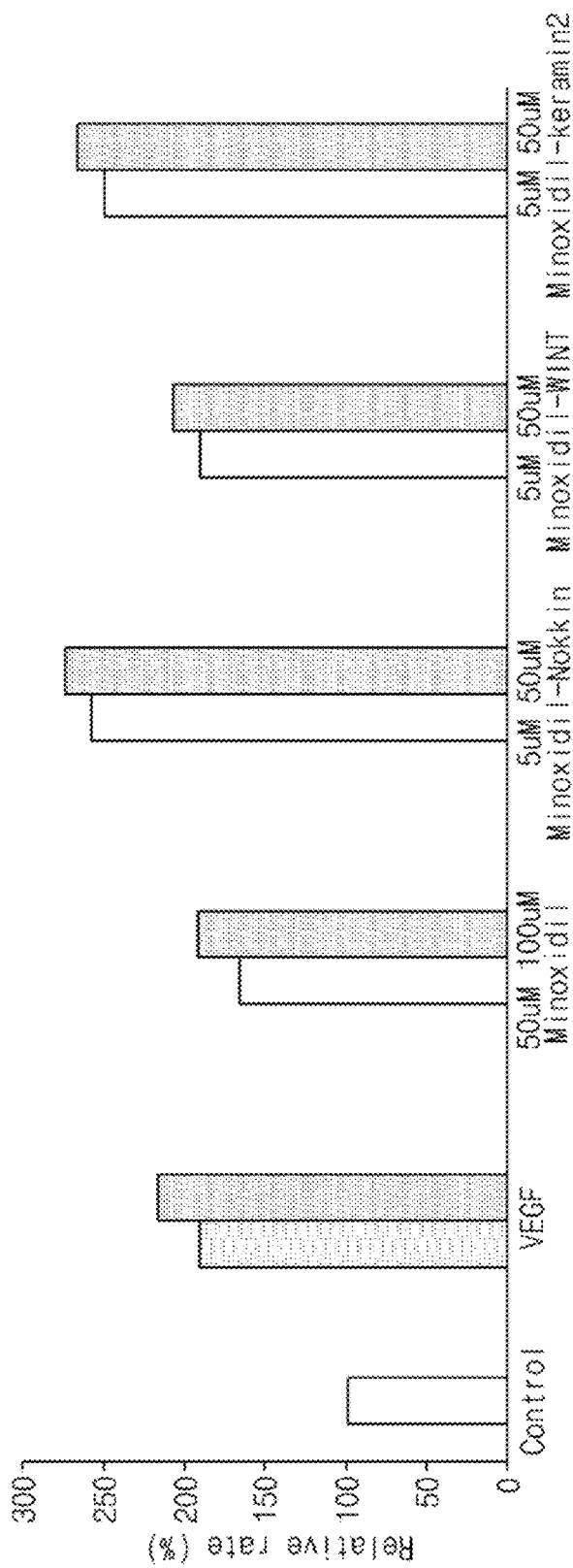
FIG. 9 shows the rate of angiogenesis of the various compounds of the present invention with control.

As a result, when treating the three compounds of the present invention, the degree of angiogenesis was excellent, and especially was superior to the Minoxidil, and blood vessels were formed to a degree similar to that of VEGF treatment (see FIG. 8). When the degree of angiogenesis in each experimental group was compared with regard to the number of completely formed blood vessels within a certain unit area, the three compounds of the present invention showed relatively good angiogenesis as compared with the Minoxidil (see FIG. 9).

<Example 5> Confirmation on Whether the Minoxidil-WINT of the Present Invention Participates in the Translocation of β-Catenin, which is a Signal Pathway of WINT, to Nucleus Hair follicle dermal papilla cells were placed in each well of a 6-well plate at $1\times10^3$ cells/well. Incubation was performed in a $CO_2$ incubator for 24 hours. After replacing the medium with serum-free DMEM medium, the Minoxidil, the Minoxidil-WINT, and the WINT were added respectively to the cells at a concentration of 5 uM and 50 uM, and then incubated for 24 hours. Protein was extracted using a protein extraction kit (extraction of each of the nuclear/cytoplasmic protein). Western blotting was carried out in the same manner as in Example 3-2 except that an anti-beta-catenin antibody, an anti-HDAC antibody, an anti-alpha tubulin antibody as primary antibodies were used.

Figure 10:
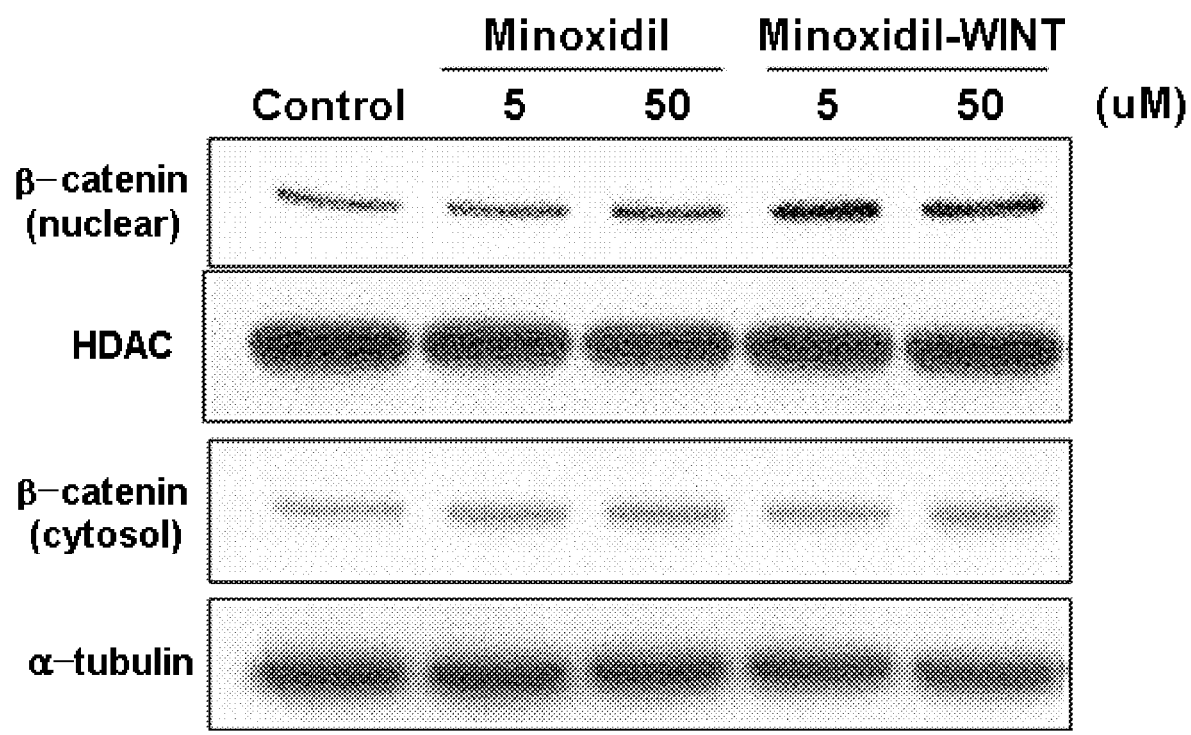
FIGS. 10 and 11 show the results of confirming the effect of the compound of the present invention on nucleus translocation of β-catenin, which is a signal pathway of WINT.
Figure 11:
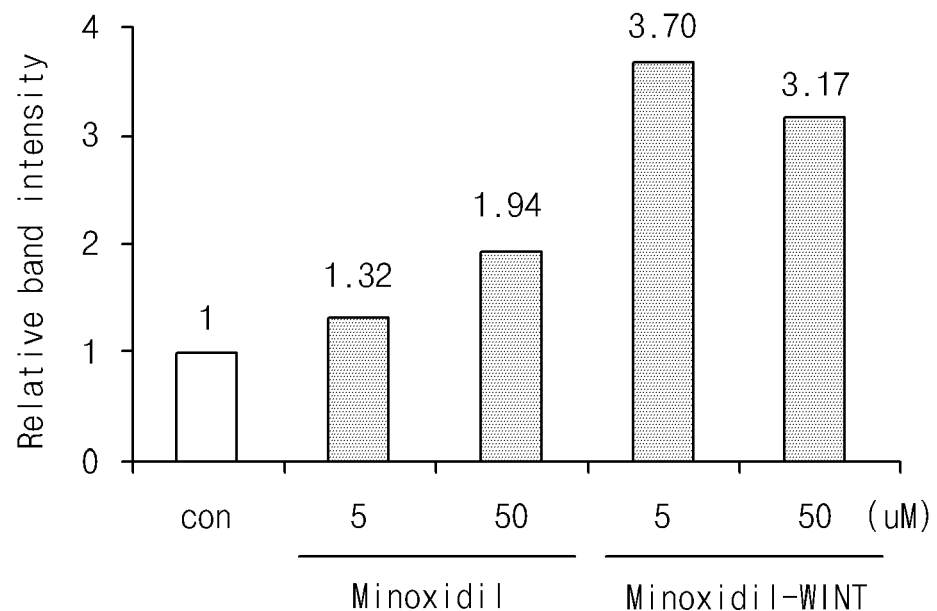

As a result, it was confirmed that the Minoxidil-WINT, a compound of the present invention, at the same concentration shows a translocation of β-catenin to the nucleus, whereas the Minoxidil alone has a significantly lower degree of translocation of β-catenin to the nucleus (see FIG. 10). The translocation of the Minoxidil-WINT to the nucleus was found to be at least 2.8-fold higher than the Minoxidil alone (see FIG. 11). From these results, it can be seen that since the Minoxidil-WINT, a compound of the present invention, can transfer β-catenin, which is a signal pathway of WINT, into the nucleus and has a higher degree of translocation of β-catenin to the nucleus than the Minoxidil, the compound of the present invention can be used for hair growth promotion or hair loss prevention.

<Example 6> Confirmation on Whether the Minoxidil-Nokkin of the Present Invention Participates in the Translocation of Phospho-Smad1/5/8, which is a Signal Pathway of Nokkin, to Nucleus It was confirmed, on whether the Minoxidil-Nokkin of the present invention inhibits the BMP signal pathway which is a major factor in hair loss, by the inhibition of phospho-Smad1/5/8 activation (migration from the cytoplasm to the nucleus). The experiment was carried out in the same manner as in Example 5, except that in the presence of BMP2, the Minoxidil-Nokkin is used instead of the Minoxidil-WINT, and an anti-P-Smad1/5/8 antibody and an anti-HDAC1 antibody were used as primary antibodies.

Figure 12:
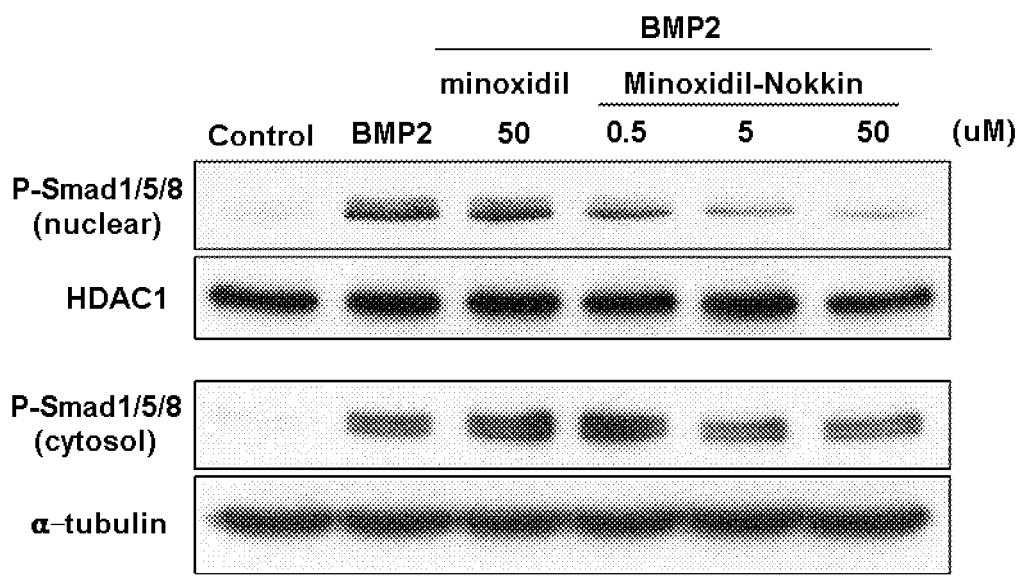
FIG. 12 shows the results of confirming whether the compound of the present invention inhibits the BMP signal pathway which is a major factor of hair loss, by the inhibition of phospho-Smad1/5/8 activation (migration from the cytoplasm to the nucleus).
Figure 13:
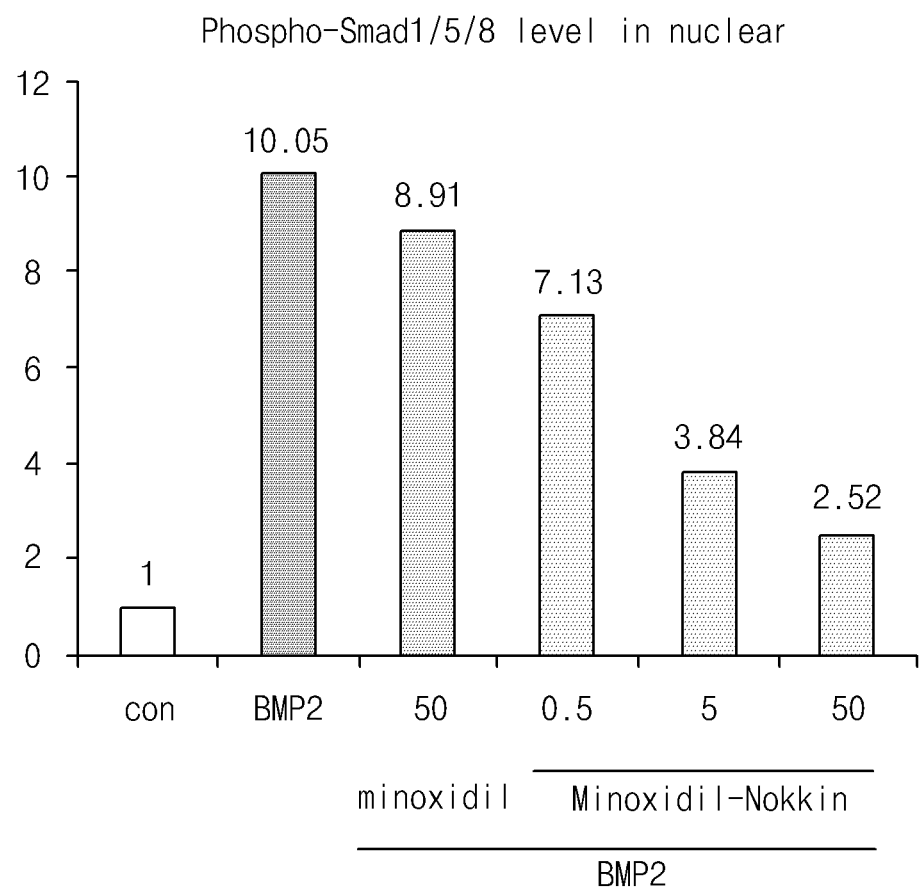
FIG. 13 shows the level of phospho-Smad1/5/8 in nucleus, confirming whether the compound of the present invention inhibits the BMP signal pathway by the inhibition of phospho-Smad1/5/8 activation (migration from the cytoplasm to the nucleus).

As a result, it was confirmed that in the case of the treatment with the Minoxidil-Nokkin, the delivery of P-Smad1/5/8 into the nucleus was reduced as compared to the treatment with the Minoxidil, and as the concentration of the Minoxidil-Nokkin is increased, P-Smad1/5/8 in the nucleus was further decreased (see FIGS. 12 and 13). From these results, it can be seen that since the Minoxidil-Nokkin of the present invention can block the BMP signal pathway to hair loss, the Minoxidil-Nokkin of the present invention can be used for hair growth promotion or hair loss prevention.

<Example 7> Identification of Hair Growth when Treating with the Compound of the Present Invention The Minoxidil-Nokkin of the present invention was applied to 6 male C57BL mice at 7 weeks of age to determine the degree of hair growth. The hair on the back of 7 weeks old C57BL/6 mice was depilated using a hair removal cream. The Minoxidil and the Minoxidil-Nokkin were added to PBS at concentrations of 100 ug/ml, respectively, to prepare a sample. The sample was applied to the dorsal skin of the mouse evenly once a day. After observing on whether the hair on the dorsal skin of the mouse was grown, photographs were taken from the point where the color of the dorsal skin was changed to black. For the histological examination, mice were slaughtered, the dorsal skins of mice were collected, fixed in 4% PFA, and embedded in paraffin. The embedding block was sectioned at 4 μm, stained with H&E and the hair follicle was observed.

Figure 14:
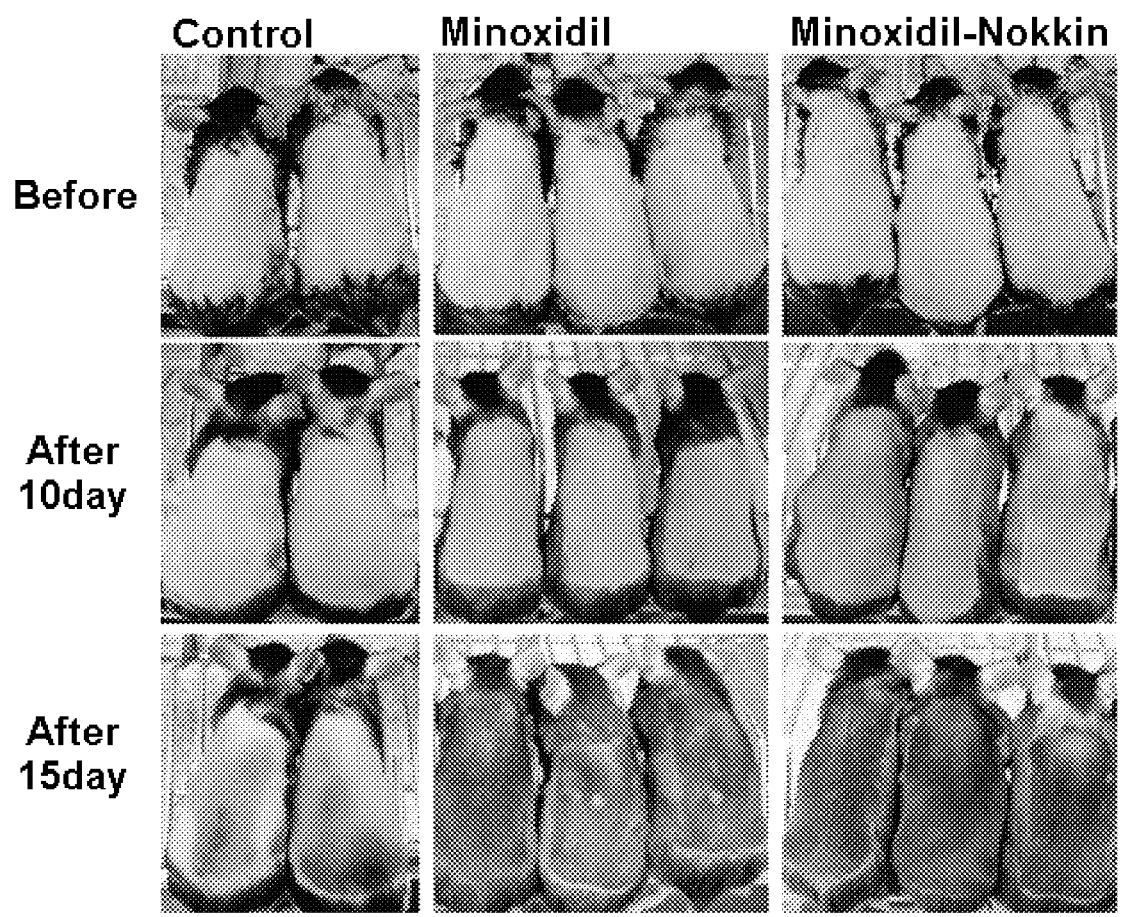
FIG. 14 shows results of confirming the degree of hair growth when treated with the compound of the present invention.
Figure 15:
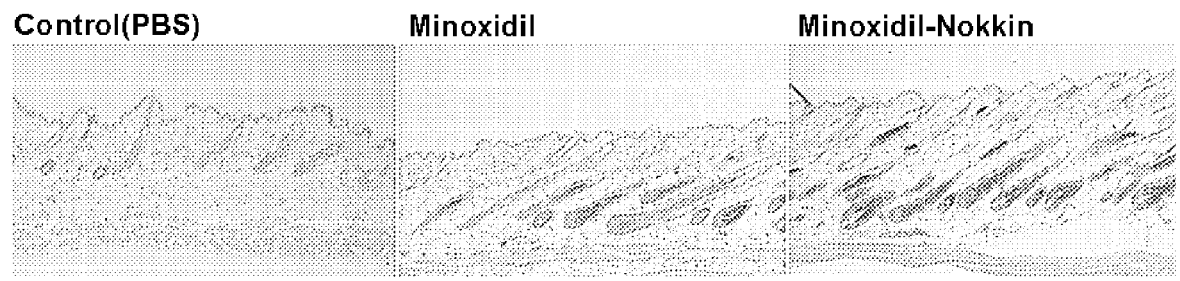
FIG. 15 shows results confirming that the hair root in the hair follicle grows long and grows onto the surface of the skin.

As a result, it was confirmed that when the compound of the present invention was applied, the hair growth rate was remarkably faster than that of the control group not treated with the sample or the group treated with the Minoxidil (see FIG. 14). When the hair follicle was examined by the H&E test, it was confirmed that in the case of the group treated with the compound of the present invention, the hair follicle was deeply located in the skin and the number of hair follicles was larger as compared with the control or the Minoxidil treated group, and the growth and development of hair follicles are promoted in a form in which the hair root in the hair follicle grows long and grows onto the surface of the skin (see FIG. 15). From the above results, it can be seen that the compound of the present invention can be used for hair growth promotion or hair loss prevention.

Formulation Example

Formulation Example 1: Emollient Beauty Wash

An emollient beauty wash comprising the compound of the present invention prepared in the above Example 1-2 and having the following composition was prepared according to a preparation method of a general beauty wash.

TABLE 3

| Component | Content(wt. %) |
|---|---|
| Compound of the present invention | 2.5 |
| 1,3-Butylene glycol | 6 |
| Glycerine | 4 |
| PEG 1500 | 1 |
| Sodium hyaluronate | 1 |
| Polysorbate 20 | 0.5 |
| Ethanol | 8 |
| Antiseptics, Coloring agents | q.s. |
| Benzophenone-9 | 0.05 |
| Perfumes | Trace |
| Purified water | Remainder |
| Total | 100 |

Formulation Example 2. Nutrition Cream

A nutrition cream comprising the compound of the present invention prepared in the above Example 1-2 and having the following composition was prepared according to a preparation method of a general nutrition cream.

TABLE 4

| Component | Content(wt. %) |
|---|---|
| Compound of the present invention | 2.5 |
| Meadowfoam oil | 3 |
| Cetearyl alcohol | 1.5 |
| Stearic acid | 1.5 |
| Glyceryl stearate | 1.5 |
| Liquid paraffin | 10 |
| Beeswax | 2 |
| Polysorbate 60 | 0.6 |
| Sorbitan sesquioleate | 2.5 |
| Squalane | 3 |
| 1,3-Butylene glycol | 3 |
| Glycerine | 5 |
| Triethanolamine | 0.5 |
| Tocopheryl acetate | 0.5 |
| Antiseptics, Coloring agents | q.s. |
| Perfumes | q.s. |
| Purified water | Remainder |
| Total | 100 |

Formulation Example 3. Nutrition Beauty Wash

A nutrition beauty wash comprising the compound of the present invention prepared in the above Example 1-2 and having the following composition was prepared according to a preparation method of a general beauty wash.

TABLE 5

| Component | Content(wt. %) |
|---|---|
| Compound of the present invention | 2.5 |
| 1,3-Butylene glycol | 4 |
| Glycerine | 4 |
| Cetearyl alcohol | 0.8 |
| Glyceryl stearate | 1 |
| Triethanolamine | 0.13 |
| Tocopheryl acetate | 0.3 |
| Liquid paraffin | 5 |
| Squalane | 3 |
| Macadamia nut oil | 2 |
| Polysorbate 60 | 1.5 |
| Sorbitan sesquioleate | 0.5 |
| Carboxyvinyl polymer | 1 |
| Antiseptics, Coloring agents | q.s. |
| Perfumes | q.s. |
| Purified water | Remainder |
| Total | 100 |

Formulation Example 4. Essence

An essence comprising the compound of the present invention prepared in the above Example 1-2 and having the following composition was prepared according to a preparation method of a general essence.

TABLE 6

| Component | Content(wt. %) |
|---|---|
| Compound of the present invention | 2.5 |
| Glycerine | 10 |
| 1,3-Butylene glycol | 5 |
| PEG 1500 | 2 |

TABLE 6-continued

| Component | Content(wt. %) |
|---|---|
| Allantoin | 0.1 |
| DL-Panthenol | 0.3 |
| EDTA-2Na | 0.02 |
| Hydroxyethyl cellulose | 0.1 |
| Sodium hyaluronate | 8 |
| Carboxyvinyl polymer | 0.2 |
| Triethanolamine | 0.18 |
| Octyldodeceth-16 | 0.4 |
| Ethanol | 6 |
| Perfumes, Antiseptics, Coloring agents | q.s. |
| Purified water | Remainder |
| Total | 100 |

Formulation Example 5. Hair Serum

A hair serum comprising the compound of the present invention prepared in the above Example 1-2 and having the following composition was prepared according to a preparation method of a general hair serum.

TABLE 7

| Component | Content(wt. %) |
|---|---|
| Compound of the present invention | 1 |
| Glycerine | 10 |
| 1,3-Butylene glycol | 5 |
| PEG 1500 | 2 |
| Allantoin | 0.1 |
| DL-Panthenol | 0.3 |
| EDTA-2Na | 0.02 |
| Hydroxyethyl cellulose | 0.1 |
| Sodium hyaluronate | 8 |
| Carboxyvinyl polymer | 0.2 |
| Triethanolamine | 0.18 |
| Octyldodeceth-16 | 0.4 |
| Ethanol | 6 |
| Perfumes, Antiseptics, Coloring agents | q.s. |
| Purified water | Remainder |
| Total | 100 |

Formulation Example 6. Hair Toner

A hair toner comprising the compound of the present invention prepared in the above Example 1-2 and having the following composition was prepared according to a preparation method of a general hair toner.

TABLE 8

| Component | Content(wt. %) |
|---|---|
| Compound of the present invention | 1 |
| Glycerine | 2 |

TABLE 8-continued

| Component | Content(wt. %) |
|---|---|
| 1,3-Butylene glycol | 2 |
| PEG 1500 | 2 |
| Allantoin | 0.1 |
| DL-Panthenol | 0.3 |
| EDTA-2Na | 0.02 |
| Sodium hyaluronate | 8 |
| Carboxyvinyl polymer | 0.2 |
| Triethanolamine | 0.18 |
| Ethanol | 10 |
| Perfumes, Antiseptics, Coloring agents | q.s. |
| Purified water | Remainder |
| Total | 100 |

While the preferred embodiments of the present invention have been illustrated by way of example, the scope of the present invention is not limited to the specific embodiments described above. Those skilled in the art will appreciate that various modifications may be made without departing from the scope of the claims of the present invention.

What is claimed is:

1. A compound represented by the following structure:

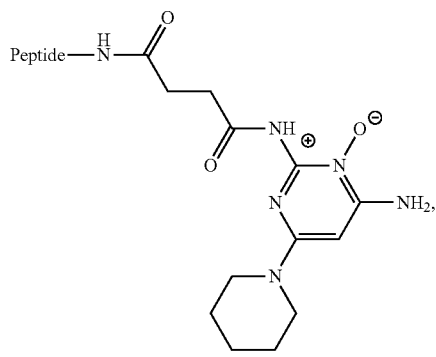

wherein the peptide is a water-soluble peptide that is 5 to 20 amino acids in length and has a ratio of hydrophilic side chain-containing amino acid of no less than 70%, and wherein the hydrophilic side chain-containing amino acid is selected from the group consisting of arginine (Arg), histidine (His), lysine (Lys), asparaginic acid (Asp), glutamic acid (Glu), serine (Ser), threonine (Thr), asparagine (Asn), glutamine (Gln), cysteine (Cys), selenocysteine (Sec), glycine (Gly) and proline (Pro).

2. The compound according to claim 1, wherein the peptide is 8 to 15 amino acids in length.

3. The compound according to claim 1, wherein the water-soluble peptide has a ratio of hydrophilic side chain-containing amino acids of no less than 90%.

4. The compound according to claim 1, wherein the water-soluble peptide has 5 or less hydrophobic side chain-containing amino acids, and the hydrophobic side chain-containing amino acid is selected from the group consisting of alanine (Ala), valine (Val), isoleucine (Ile), leucine (Leu), methionine (Met), phenylalanine (Phe), tyrosine (Tyr) and tryptophan (Trp).

5. The compound according to claim 4, wherein the water-soluble peptide has 3 or less hydrophobic side chain-containing amino acids.

6. The compound according to claim 1, wherein the peptide is selected from the group consisting of nokkin peptide consisting of the amino acid sequence of SEQ ID NO: 1; keramin2 peptide consisting of the amino acid sequence of SEQ ID NO: 2; and WINT peptide consisting of the amino acid sequence of SEQ ID NO: 3.

7. A pharmaceutical composition for hair loss treatment or hair growth promotion comprising the compound of claim 1.

8. A cosmetic composition for hair loss treatment or hair growth promotion comprising the compound of claim 1.

9. The cosmetic composition according to claim 8, wherein the cosmetic composition is a formulation selected from the group consisting of emollient beauty wash, nutrition beauty wash, nutrition cream, massage cream, essence, eye cream, cleansing cream, cleansing foam, cleansing water, pack, spray, powder, hair tonic, hair cream, hair lotion, hair shampoo, hair rinse, hair conditioner, hair-spray, hair air-sol, pomade, sol-gel, emulsion, oil, wax and air-sol.

10. A method for treating hair loss or promoting hair growth comprising the step of transdermally administering the compound of claim 1 to the affected part of the individual suffering from hair loss.

* * * * *

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: nokkin peptide

<400> SEQUENCE: 1

Glu Leu Ile Glu His Gly Gly Gly Arg Pro Ala Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: keramin2 peptide

<400> SEQUENCE: 2

Tyr Lys Ser Lys Lys Gly Gly Trp Thr His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: WINT peptide

<400> SEQUENCE: 3

Arg Gln Thr Arg Val Gln Arg Cys His Cys
1               5                   10

<210> SEQ ID NO 4
<211> LENGTH: 21
<212> TYPE: DNA
<213> ORGANISM: Artificial Sequence
<220> FEATURE:
<223> OTHER INFORMATION: VEGF Forward

<400> SEQUENCE: 4
ccatgaactt tctgctgtct t                                             21

<210> SEQ ID NO 5
<211> LENGTH: 21
<212> TYPE: DNA
<213> ORGANISM: Artificial Sequence
<220> FEATURE:
<223> OTHER INFORMATION: VEGF Reverse

```
<400> SEQUENCE: 5
tcgatcgttc tgtatcagtc t                                              21

<210> SEQ ID NO 6
<211> LENGTH: 21
<212> TYPE: DNA
<213> ORGANISM: Artificial Sequence
<220> FEATURE:
<223> OTHER INFORMATION: TGFb1 Forward

<400> SEQUENCE: 6
gccctggata ccaactattg c                                              21

<210> SEQ ID NO 7
<211> LENGTH: 21
<212> TYPE: DNA
<213> ORGANISM: Artificial Sequence
<220> FEATURE:
<223> OTHER INFORMATION: TGFb1 Reverse

<400> SEQUENCE: 7
tcagcacttg caggagtagc g                                              21

<210> SEQ ID NO 8
<211> LENGTH: 20
<212> TYPE: DNA
<213> ORGANISM: Artificial Sequence
<220> FEATURE:
<223> OTHER INFORMATION: GAPDH Forward

<400> SEQUENCE: 8
ggagccaaaa gggtcatcat                                                20

<210> SEQ ID NO 9
<211> LENGTH: 20
<212> TYPE: DNA
<213> ORGANISM: Artificial Sequence
<220> FEATURE:
<223> OTHER INFORMATION: GAPDH Reverse

<400> SEQUENCE: 9
gtgatggcat ggactgtggt                                                20
```